(12) United States Patent
Winn et al.

(10) Patent No.: US 10,337,068 B2
(45) Date of Patent: Jul. 2, 2019

(54) TRPC6 INVOLVED IN GLOMERULONEPHRITIS

(71) Applicant: Duke University, Durham, NC (US)

(72) Inventors: Michelle Winn, Durham, NC (US); Margaret A. Pericak-Vance, Coral Gables, FL (US); Jeffery M. Vance, Coral Gables, FL (US)

(73) Assignee: DUKE UNIVERSITY, Durham, NC (US)

( * ) Notice: Subject to any disclaimer, the term of this patent is extended or adjusted under 35 U.S.C. 154(b) by 269 days.

(21) Appl. No.: 15/170,916

(22) Filed: Jun. 1, 2016

(65) Prior Publication Data

US 2016/0376655 A1 Dec. 29, 2016

Related U.S. Application Data

(60) Continuation of application No. 12/782,075, filed on May 18, 2010, now Pat. No. 9,433,642, which is a continuation of application No. 11/716,050, filed on Mar. 9, 2007, now Pat. No. 7,745,597, which is a division of application No. 11/417,113, filed on May 4, 2006, now abandoned.

(60) Provisional application No. 60/677,825, filed on May 5, 2005.

(51) Int. Cl.
| | |
|---|---|
| *A61K 31/69* | (2006.01) |
| *A61K 33/24* | (2019.01) |
| *A61K 38/00* | (2006.01) |
| *G01N 33/68* | (2006.01) |
| *C07K 14/705* | (2006.01) |
| *C12Q 1/6883* | (2018.01) |
| *A61K 31/4174* | (2006.01) |

(52) U.S. Cl.
CPC ........ *C12Q 1/6883* (2013.01); *A61K 31/4174* (2013.01); *A61K 31/69* (2013.01); *A61K 33/24* (2013.01); *C07K 14/705* (2013.01); *G01N 33/6872* (2013.01); *A61K 38/00* (2013.01); *C12Q 2600/118* (2013.01); *C12Q 2600/136* (2013.01); *C12Q 2600/156* (2013.01); *C12Q 2600/158* (2013.01); *G01N 2333/705* (2013.01); *G01N 2500/04* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,745,597 B2 | 6/2010 | Winn et al. |
| 7,964,573 B2 | 6/2011 | Remillard et al. |
| 2003/0144191 A1 | 7/2003 | Lee et al. |
| 2003/0186273 A1 | 10/2003 | Galvin |
| 2004/0023873 A1 | 2/2004 | Florman et al. |
| 2004/0092475 A1 | 5/2004 | Li et al. |
| 2006/0257500 A1 | 11/2006 | Winn et al. |

OTHER PUBLICATIONS

Pocock, "Evidence of a Role for TRPC Channels in VEGF-Mediated Increased Vascular Permeability in Vivo," Am. J. Physiol. Heart Circ. Physiol., Mar. 2004; 286(3): H1015-36. Epub Oct. 9, 2003 (abstract).
Jung, "TRPC6 is a Candidate Channel Involved in Receptor-Stimulated Cation Currents in A7r5 Smooth Muscle Cells," Am. J. Physiol., Feb. 2002; 282(2): C347-59 (Abstract).
Xu, "Block of TRPC5 Channels by 2-Aminoethosydiphenyl Borate: A Differential, Extracellular and Voltage-Dependent Effect," Br J. Pharmacol., Apr. 4, 2005 [Epub ahead of print].
S. Thebault, et al., "Receptor-Operated Ca2+ Entry Mediated by TRPC3/TRPC6 Proteins in Rat Prostate Smooth Muscle (PS1) Cell Line," Journal of Cellular Physiology, 2004: 320-328 (2005).
NM_004621; GenBank; *Homo sapiens* tran ... [gi: 19923256] (Apr. 23, 2005) (author not available).
GeneID: 7225 Locus tag: HGNC: 12338; MIM: 603652; NCBI Entrez Gene (author and date not available).
Winn, "A Mutation in the TRPC6 Cation Channel Causes Familial Focal Segmental Glomerulosclerosis," Abstract SA-FC054, Free Communication, St. Louis MO. 37th Annual American Society of Nephrology Meeting, 2004.
SNP Linked to Gene (geneID:7225); NCBI Single Nucleotide Polymorphism (author and date not available).
Winn, M.P., et al. "Clinical and Genetic Heterogeneity in Familial Focal Segmental Glomerulosclerosis," Kidney International 55: 1241-1246 (1999) (month not available).
Winn, M.P., et al., "Linkage of a Gene Causing Familial Focal Segmental Glomerulosclerosis to Chromosome 11 and Further Evidence of Genetic Heterogeneity," Genomics, 58: 113-120 (Mar. 1999).
Reiser, J., et al., "TRPC6 is a Glomerular Slit Diaphragm-Associated Channel Required for Normal Renal Function," Nat. Genet. 37(7):739-744 (Jul. 2005).

(Continued)

*Primary Examiner* — Paul J Holland
(74) *Attorney, Agent, or Firm* — Foley & Lardner LLP

(57) ABSTRACT

Focal and segmental glomerulosclerosis (FSGS) is a kidney disorder of unknown etiology and up to 20% of patients on dialysis have this diagnosis. A large family with hereditary FSGS carries a missense mutation in the TRPC6 gene on chromosome 11q, encoding the ion channel protein Transient Receptor Potential Cation Channel 6. The missense mutation is a P112Q substitution, which occurs in a highly conserved region of the protein, enhances TRPC6-mediated calcium signals in response to agonists such as angiotensin II, and alters the intracellular distribution of TRPC6 protein. Previous work has emphasized the importance of cytoskeletal and structural proteins in proteinuric kidney diseases. Our findings suggest a novel mechanism for glomerular disease pathogenesis.

8 Claims, 29 Drawing Sheets
Specification includes a Sequence Listing.

(56) References Cited

OTHER PUBLICATIONS

Freichel, M., et al., "Functional Role of TRPC Proteins in Vivo: Lessons from TRPC-Deficient Mouse Models," Biochem. and Biophys. Res. Commun. 322:1352-1358 (Aug. 2004).
U.S. Office Action dated Mar. 22, 2007 for U.S. Appl. No. 11/417,113.
U.S. Office Action dated Sep. 24, 2007 for U.S. Appl. No. 11/417,113.
U.S. Office Action dated Jan. 11, 2008 for U.S. Appl. No. 11/417,113.
U.S. Office Action dated Jul. 30, 2009 for U.S. Appl. No. 11/716,050.
Yip et al., "Expression of TRPC homologs in endothelial cells and smooth muscle layers of human arteries," Histochem. Cell. Biol., vol. 122, pp. 553-561 (2004).
Winn et al., "A Mutation in the TRPC6 Cation Channel Causes Familial Focal Segmental Glomerulosclerosis," Science, vol. 308, pp. 1801-1804 (2005).
Conlon et al., "Spectrum of Disease in Familial Focal and Segemental Glomerulosclerosis," Kidney International, vol. 56, pp. 1863-1871 (1999).

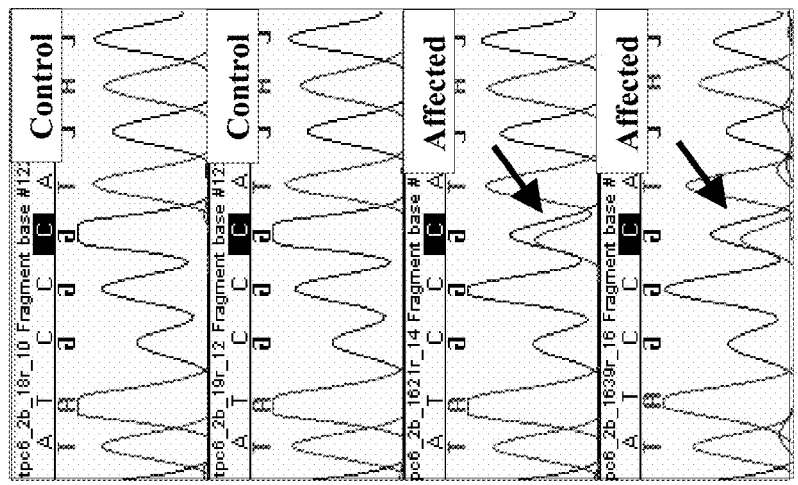

FIG. 5

```
                              80            *           100           *           120           *           140           *
Homo sapiens              : RLANRG--PAYMFSDRSTSLSIEEERFLDAAEHYGNIPVVRKMLEECHS---LNVNCVDYMGQNALQLAVANEHLEIT
Mus musculus              : RLANRG--PAYMFNDHSTSLSIEEERFLDAVEYGNIPVVWKMLEECHS---LNVNCVDYMGQNALQLAVANEHLEIT
Rattus norvegicus         : RLANRG--PAYMFNDHSTSLSIEEERFLDAAEHYGNIPVVRKMLEECLS---LNVNCVDYMGQNALQLAVANEHLEIT
Cavia porcellus           : RLANRG--PAYMFNDHSTTLSIEEERFLDAAEHYGNIPVVRKMLEECLS---LNVNCVDYMGQNALQLAVANEHLEIT
Drosophila melanogaster   : APKSVG--GCCVPLGLPQPLLLEKKFLLAVERGDMPNVRRILQKALRHQHINICMDPLGRRALTLAIDNENLEMV
Caenorhabditis elegans    : RKSRVKSLKHAQLLHGYYILSNNLFRFLEAAELGNKPTLQECLDYDGDRR-LNVNCLDSMGRTALEIAVDNENMEVV
```

FIG. 9

Table 1 – Primer sequences for *TRPC6*.

| Primer Name | Melting Temp | Product Size | Primer Sequence |
|---|---|---|---|
| TRPC6_1F | 74.52 | 394 | cctcctagttcaggctcataccgcctcctg |
| TRPC6_1R | 77.00 | | acgacggtgaagcagggggtgcaga |
| TRPC6_1bF | 73.90 | 492 | taagtggtgactttccccgggccagt |
| TRPC6_1bR | 73.43 | | cctaggaggtacacacgcgggttcagg |
| TRPC6_2aF | 59.64 | 439 | gcaaagtgcttggctttctt |
| TRPC6_2aR | 60.16 | | cattctgcccatgtaatcc |
| TRPC6_2bF | 60.62 | 323 | cgtgagaaggggagaaggtt |
| TRPC6_2bR | 59.94 | | attgcttccacaatccgaac |
| TRPC6_2cF | 58.88 | 310 | agaatgccactcactcaacg |
| TRPC6_2cR | 60.05 | | tggagtcacatcatgggaga |
| TRPC6_2dF | 59.94 | 292 | gttcggattgtggaagcaat |
| TRPC6_2dR | 59.44 | | tggagtggctaaacgagtca |
| TRPC6_2eF | 59.47 | 336 | ctcccatgatgtgactccaa |
| TRPC6_2eR | 59.3 | | gcttgtggagggtgaagtct |
| TRPC6_2fF | 59.44 | 233 | tgactcgtttagccactcca |
| TRPC6_2fR | 60.2 | | ctgagcacatgggggaag |
| TRPC6_3F | 58.03 | 313 | tctgaagcatagtaaaacgtggt |
| TRPC6_3R | 59.79 | | cccttatccttatttagcaccaa |
| TRPC6_4F | 60.93 | 427 | gccatttgtttgttgcctgt |
| TRPC6_4R | 60.36 | | acccaactgtgattccctga |
| TRPC6_5F | 60.48 | 490 | ggagatcattggaatgtgcag |
| TRPC6_5R | 59.45 | | aatgaacccaaggcaactgt |
| TRPC6_6F | 60.42 | 406 | caggctgagacctttcaaaca |
| TRPC6_6R | 57.73 | | tgcagtaaccgaactactactgac |
| TRPC6_7aF | 59.93 | 361 | ggagacttccattcgaaaacc |
| TRPC6_7aR | 57.68 | | tgcaccaatgtagtaggagtagag |
| TRPC6_7bF | 59.99 | 414 | ggacccctctgatcctcaa |
| TRPC6_7bR | 59.11 | | agagtccctccaactcatttgt |
| TRPC6_8F | 61.13 | 490 | ccatccttgcagcaatccta |
| TRPC6_8R | 60.19 | | gaatgaacaaagggcgaaga |
| TRPC6_9F | 60.82 | 400 | cgatcactggggtctgagag |
| TRPC6_9R | 59.81 | | aaagggatgtggcatagtgg |
| TRPC6_10F | 59.93 | 290 | agggaagaacccgtaagaa |
| TRPC6_10R | 59.76 | | gcttctgaacatctgtccctt |
| TRPC6_11F | 59.52 | 457 | ctcagacaacctctaacaaacagc |
| TRPC6_11R | 58.35 | | caaaatgcctggtacatggt |
| TRPC6_12F | 58.89 | 250 | ggctcactacagggaggaag |
| TRPC6_12R | 59.81 | | gctctccaggcactctgc |
| TRPC6_13aF | 60.09 | 316 | tttcctcctgtcccacagtc |
| TRPC6_13aR | 60.07 | | gcccattggcacttaagaaa |
| TRPC6_13bF | 59.96 | 430 | tctccgctatgaactccttga |
| TRPC6_13bR | 59.97 | | acccatttcaggcagacac |
| TRPC6_13cF | 59.06 | 273 | ggcccacctttaaacaaga |
| TRPC6_13cR | 61.1 | | aaaaccgcatggggagtaac |
| TRPC6_13dF | 58.9 | 348 | tgttcagggtaaaggctgtaga |
| TRPC6_13dR | 59.05 | | tgcattgagggataagtaggg |
| TRPC6_13eF | 59.85 | 300 | tgcggttttcctctgaagt |
| TRPC6_13eR | 58.98 | | catgtttcagggttcagtg |
| TRPC6_13fF | 59.86 | 347 | ccctacttatccctcaatgcac |
| TRPC6_13fR | 58.88 | | tggaaccaaacaaccacagt |
| TRPC6_13gF | 59.67 | 481 | ttttgtgtgtgtgcgtgtgt |
| TRPC6_13gR | 60.07 | | cctctgaatgccaatggtct |
| TRPC6_13hF | 60.04 | 389 | gccatttctgggagcattta |
| TRPC6_13hR | 59.03 | | gccaaagttggagctaaacag |
| TRPC6_13jF | 57.64 | 470 | ctgatcatgtgaagtggtgtct |
| TRPC6_13jR | 59.61 | | ggatgaaggtccatctctcg |

Fig. 10. Table 2.

Gene Model (mRNA alignment) information from genome sequence

Total gene model (contig mRNA transcript): 1

| Contig | mrna | protein | mrna orientation | transcript | snp list |
|---|---|---|---|---|---|
| NT_033899 | NM_004621 | NP_004612 | reverse | minus strand | currently shown |

[view rs] ☐ in gene region ☒ cSNP ☐ has frequency ☐ double hit ☐ haplotype tagged

| gene model (contig mRNA transcript): | Contig | mrna | protein | mrna orientation | transcript | snp count |
|---|---|---|---|---|---|---|
| | NT_033899 | NM_004621 | NP_004612 | reverse | minus strand | 3, coding |

| Contig position | dbSNP rs# cluster id | Hetero- zygosity | Validation | 3D | OMIM | Function | dbSNP allele | Protein residue | Codon position | Amino acid position |
|---|---|---|---|---|---|---|---|---|---|---|
| 4886186 | rs12805398 | N.D. | | | | synonymous | A | Gln [Q] | 3 | 904 |
| | | N.D. | | | | contig reference | G | Gln [Q] | 3 | 904 |
| 4909509 | rs12366144 | 0.399 | | | | synonymous | C | Asn [N] | 3 | 561 |
| | | 0.399 | | | | contig reference | T | Asn [N] | 3 | 561 |
| 5016608 | rs3802829 | N.D. | | | | nonsynonymous | T | Ser [S] | 1 | 15 |
| | | N.D. | | | | contig reference | C | Pro [P] | 1 | 15 |

Variations in genomic region of TRPC6

| Contig Accession | Contig position | dbSNP rs# cluster id | Hetero- zygosity | Validation | 3D | OMIM | Function | dbSNP allele | Protein residue | Codon position | Amino acid position |
|---|---|---|---|---|---|---|---|---|---|---|---|
| NT_033899 | 5017494 | rs5794116 | N.D. | | | | locus | | | | |
| NT_033899 | 5017564 | rs3922961 | N.D. | | | | locus | | | | |
| NT_033899 | 5018318 | rs5794117 | N.D. | | | | locus | | | | |

Fig. 10. Table 2. (Continued)

| | | | | | |
|---|---|---|---|---|---|
| NT_033899 | 5018319 | rs5794118 | N.D. | | locus |
| NT_033899 | 5018321 | rs5015415 | N.D. | | locus |
| NT_033899 | 5018357 | rs10667425 | N.D. | | locus |
| NT_033899 | 5018365 | rs3842259 | N.D. | | locus |
| NT_033899 | 5018418 | rs3824935 | 0.255 |  | locus |
| NT_033899 | 5018468 | rs3842260 | N.D. | | locus |

Snp linked to TRPC6 from GenBank  

Click here to turn on the view of snp from GenBank. This will turn off the view of snp in Contig Annotation.

GENERAL: Contact Us | Homepage | Announcements |dbSNP Summary | Genome | FTP SERVER | Build History | Handle Request
DOCUMENTATION: FAQ | Overview | How to Submit | RefSNP Summary Info | Database Schema
SEARCH: Entrez SNP | Blast SNP | Main Search |Batch Query | By Submitter |New Batches | Method | Population | Publication
| Chromosome Report | Batch |Locus Info | Free Form | Easy Form | Between Marker
HAPLOTYPE: Specifications | Sample HapSet | Sample Individual
NCBI: PubMed | Entrez | BLAST | OMIM | Taxonomy | Structure Disclaimer   Privacy statement Revised: June 9, 2004 8:18 AM.

Fig. 11. Table 3.

| Contig position | dbSNP rs# cluster id | Hetero-zygosity | Validation | 3D | OMIM | Function | dbSNP allele | Protein residue | Codon position | Amino acid position |
|---|---|---|---|---|---|---|---|---|---|---|
| 4885393 | rs10634011 | N.D. | | | | untranslated | | | | |
| 4885549 | rs7931399 | 0.413 | ✻ | | H | untranslated | | | | |
| 4886186 | rs12805398 | N.D. | | | | synonymous | A | Gln [Q] | 3 | 904 |
| | | N.D. | | | | contig reference | G | Gln [Q] | 3 | 904 |
| 4886273 | rs10570417 | N.D. | | | | intron | | | | |
| 4886399 | rs12804391 | N.D. | | | | intron | | | | |
| 4887262 | rs10444351 | N.D. | | | | intron | | | | |
| 4887986 | rs11301008 | N.D. | | | | intron | | | | |
| 4887994 | rs7121124 | N.D. | ✻ | | | intron | | | | |
| 4888386 | rs7105083 | N.D. | ✻ | | | intron | | | | |
| 4888535 | rs7928028 | N.D. | ✻ | | | intron | | | | |
| 4888742 | rs4405276 | 0.418 | ✻ | | H | intron | | | | |
| 4889932 | rs7110162 | N.D. | ✻ | | | intron | | | | |
| 4890043 | rs7480272 | N.D. | | | | intron | | | | |
| 4890218 | rs4489713 | N.D. | ✻ | | | intron | | | | |
| 4890473 | rs4522135 | N.D. | ✻ | | | intron | | | | |
| 4890922 | rs6590860 | N.D. | ✻ | | | intron | | | | |
| 4891067 | rs7126090 | N.D. | | | | intron | | | | |
| 4891328 | rs11224768 | N.D. | | | | intron | | | | |
| 4891591 | rs7950048 | N.D. | ✻ | | | intron | | | | |
| 4892126 | rs6590861 | N.D. | ✻ | | | intron | | | | |
| 4892293 | rs12289447 | N.D. | | | | intron | | | | |
| 4892400 | rs11826762 | N.D. | ✻ | | | intron | | | | |
| 4892506 | rs11822237 | N.D. | ✻ | | | intron | | | | |
| 4893223 | rs4396256 | 0.424 | ✻ | | H | intron | | | | |
| 4893344 | rs11224769 | N.D. | ✻ | | | intron | | | | |
| 4895513 | rs10895110 | N.D. | | | | intron | | | | |
| 4895590 | rs10895111 | N.D. | | | | intron | | | | |
| 4895677 | rs10791473 | N.D. | | | | intron | | | | |
| 4895818 | rs10895112 | N.D. | | | | intron | | | | |
| 4895945 | rs10895113 | N.D. | | | | intron | | | | |
| 4896011 | rs11224770 | N.D. | | | | intron | | | | |
| 4896067 | rs11224771 | N.D. | | | | intron | | | | |
| 4896176 | rs10895114 | N.D. | ✻ | | | intron | | | | |
| 4896414 | rs10791474 | N.D. | ✻ | | | intron | | | | |

Fig. 11. Table 3. (Continued)

| | | | | | | | | | |
|---|---|---|---|---|---|---|---|---|---|
| 4896429 rs10791475 | N.D. | | | | intron | | | | |
| 4896606 rs7120857 | N.D. | | | | intron | | | | |
| 4896870 rs7109734 | N.D. | | | | intron | | | | |
| 4897128 rs6590862 | 0.426 | | | | intron | | | | |
| 4897398 rs7942665 | N.D. | | | | intron | | | | |
| 4897551 rs12577550 | N.D. | | | | intron | | | | |
| 4898453 rs7936768 | N.D. | | | | intron | | | | |
| 4898487 rs7947695 | N.D. | | | | intron | | | | |
| 4898960 rs12795728 | N.D. | | | | intron | | | | |
| 4899101 rs12797690 | N.D. | | | | intron | | | | |
| 4899395 rs7930422 | N.D. | | | | intron | | | | |
| 4900248 rs12804595 | N.D. | | | | intron | | | | |
| 4900784 rs4131268 | N.D. | | | H | intron | | | | |
| 4900989 rs11224772 | N.D. | | | | intron | | | | |
| 4901959 rs7940955 | 0.005 | | | H | intron | | | | |
| 4902188 rs17093587 | 0.029 | | | | intron | | | | |
| 4902373 rs12800530 | N.D. | | | | intron | | | | |
| 4902423 rs11224773 | 0.120 | | | | intron | | | | |
| 4903655 rs7935581 | 0.413 | | | H | intron | | | | |
| 4903731 rs11224774 | N.D. | | | | intron | | | | |
| 4903776 rs11224775 | N.D. | | | | intron | | | | |
| 4903877 rs11224776 | N.D. | | | | intron | | | | |
| 4903906 rs11224777 | N.D. | | | | intron | | | | |
| 4903931 rs11224778 | N.D. | | | | intron | | | | |
| 4905778 rs11224779 | 0.420 | | | | intron | | | | |
| 4906045 rs11224780 | 0.431 | | | | intron | | | | |
| 4906593 rs12362848 | 0.414 | | | | intron | | | | |
| 4907115 rs7948300 | 0.415 | | | H | intron | | | | |
| 4907450 rs7948687 | N.D. | | | | intron | | | | |
| 4907454 rs12281218 | N.D. | | | | intron | | | | |
| 4907521 rs12786558 | N.D. | | | | intron | | | | |
| 4907617 rs11822192 | N.D. | | | | intron | | | | |
| 4908827 rs11295537 | N.D. | | | | intron | | | | |
| 4908920 rs7127346 | N.D. | | | | intron | | | | |
| 4909009 rs10644636 | N.D. | | | | intron | | | | |
| 4909509 rs12366144 | 0.399 | | | | synonymous | C | Asn [N] | 3 | 561 |

Fig. 11. Table 3. (Continued)

|  |  |  |  |  |  |  |  |
|---|---|---|---|---|---|---|---|
|  | 0.399 |  |  | contig reference T | Asn [N] | 3 | 561 |
| 4910324 rs11224781 | N.D. |  |  | intron |  |  |  |
| 4910967 rs7927507 | N.D. |  |  | intron |  |  |  |
| 4912232 rs11224782 | 0.394 |  | H | intron |  |  |  |
| 4912254 rs11224783 | N.D. |  |  | intron |  |  |  |
| 4912592 rs12362157 | N.D. |  |  | intron |  |  |  |
| 4912836 rs7114045 | N.D. |  |  | intron |  |  |  |
| 4912932 rs17740759 | 0.081 |  |  | intron |  |  |  |
| 4912987 rs10539236 | N.D. |  |  | intron |  |  |  |
| 4913109 rs7925826 | N.D. |  |  | intron |  |  |  |
| 4913366 rs7130287 | N.D. |  |  | intron |  |  |  |
| 4913390 rs6590864 | N.D. |  |  | intron |  |  |  |
| 4913479 rs7115010 | N.D. |  |  | intron |  |  |  |
| 4913514 rs7103383 | N.D. |  |  | intron |  |  |  |
| 4913719 rs7118253 | N.D. |  |  | intron |  |  |  |
| 4913799 rs7117447 | N.D. |  |  | intron |  |  |  |
| 4913965 rs12791865 | N.D. |  |  | intron |  |  |  |
| 4914607 rs17673079 | 0.166 |  |  | intron |  |  |  |
| 4914843 rs10895115 | 0.495 |  |  | intron |  |  |  |
| 4915705 rs11821584 | N.D. |  |  | intron |  |  |  |
| 4915760 rs11224784 | 0.433 |  |  | intron |  |  |  |
| 4915793 rs11826165 | 0.428 |  |  | intron |  |  |  |
| 4915897 rs12361641 | 0.428 |  |  | intron |  |  |  |
| 4915908 rs11224785 | 0.431 |  |  | intron |  |  |  |
| 4916448 rs11826302 | N.D. |  |  | intron |  |  |  |
| 4916857 rs7938416 | 0.420 |  | H | intron |  |  |  |
| 4917051 rs7952474 | 0.417 |  |  | intron |  |  |  |
| 4917357 rs7924434 | N.D. |  |  | intron |  |  |  |
| 4917384 rs7924551 | N.D. |  |  | intron |  |  |  |
| 4917542 rs7942339 | 0.242 |  |  | intron |  |  |  |
| 4917736 rs10627556 | N.D. |  |  | intron |  |  |  |
| 4917747 rs10539799 | N.D. |  |  | intron |  |  |  |
| 4917754 rs10536580 | N.D. |  |  | intron |  |  |  |
| 4917759 rs10539800 | N.D. |  |  | intron |  |  |  |
| 4917772 rs10536581 | N.D. |  |  | intron |  |  |  |
| 4918273 rs10639907 | N.D. |  |  | intron |  |  |  |

Fig. 11. Table 3. (Continued)

| | | | | | |
|---|---|---|---|---|---|
| 4918282 | rs10645525 | N.D. | | | intron |
| 4918318 | rs6590865 | N.D. | ● | | intron |
| 4918426 | rs11325078 | N.D. | | | intron |
| 4918545 | rs12801419 | N.D. | | | intron |
| 4918894 | rs12577872 | N.D. | | | intron |
| 4919022 | rs7934021 | 0.433 | ✕ | ▯ | intron |
| 4919232 | rs10567537 | N.D. | | | intron |
| 4919905 | rs12270234 | N.D. | | ▯ | intron |
| 4920414 | rs12787386 | N.D. | | | intron |
| 4920499 | rs6590866 | 0.422 | ✕ | ▯ | intron |
| 4920784 | rs11398560 | N.D. | | | intron |
| 4921141 | rs7927664 | 0.422 | ✕ | ▯ | intron |
| 4921527 | rs7945727 | 0.211 | ✕ | H | intron |
| 4922348 | rs7931830 | 0.419 | ✕ | ▯H | intron |
| 4922533 | rs10611884 | N.D. | | | intron |
| 4922547 | rs7932073 | N.D. | ● | ▯ | intron |
| 4923223 | rs7935628 | N.D. | | ▯ | intron |
| 4923444 | rs12806241 | N.D. | | | intron |
| 4923982 | rs12789670 | N.D. | | ▯ | intron |
| 4924319 | rs12796163 | N.D. | | ▯ | intron |
| 4924560 | rs11224786 | N.D. | | | intron |
| 4925092 | rs12797471 | N.D. | | | intron |
| 4925113 | rs12795143 | N.D. | | | intron |
| 4925133 | rs10895116 | N.D. | | ▯ | intron |
| 4925138 | rs12796749 | N.D. | | | intron |
| 4925201 | rs12802815 | N.D. | | | intron |
| 4925237 | rs10895117 | N.D. | | ▯ | intron |
| 4925589 | rs11224787 | N.D. | | ▯ | intron |
| 4925678 | rs9326313 | N.D. | ● | ▯ | intron |
| 4926001 | rs10160655 | 0.456 | ✕ | ▯ | intron |
| 4926209 | rs10160542 | 0.456 | ✕ | ▯ | intron |
| 4926641 | rs10895118 | N.D. | ● | ▯ | intron |
| 4926919 | rs12283329 | 0.106 | ✕ | | intron |
| 4927448 | rs4129254 | 0.460 | ✕ | ▯H | intron |
| 4927573 | rs4129253 | 0.200 | ✕ | ▯H | intron |
| 4927619 | rs4129255 | 0.465 | ✕ | ▯H | intron |

Fig. 11. Table 3. (Continued)

| | | | | | |
|---|---|---|---|---|---|
| 4928118 | rs10791477 | 0.460 | ✂ | ⬚ | intron |
| 4928148 | rs10791478 | 0.459 | ✂ | ⬚ | intron |
| 4928607 | rs10895119 | N.D. | | ⬚ | intron |
| 4928768 | rs11224788 | N.D. | | | intron |
| 4928780 | rs10895120 | N.D. | | ⬚ | intron |
| 4928890 | rs10895121 | 0.456 | ✂ | ⬚ | intron |
| 4929530 | rs10895122 | 0.131 | ✂ | ⬚ | intron |
| 4929628 | rs10501979 | 0.157 | ✂ | ⬚H | intron |
| 4930135 | rs4403777 | 0.492 | ✂ | ⬚H | intron |
| 4930401 | rs12793746 | N.D. | | | intron |
| 4930589 | rs10791479 | N.D. | • | ⬚ | intron |
| 4930601 | rs10791480 | N.D. | • | ⬚ | intron |
| 4930656 | rs10791481 | N.D. | • | ⬚ | intron |
| 4930659 | rs10791482 | N.D. | • | ⬚ | intron |
| 4931039 | rs10895123 | N.D. | • | ⬚ | intron |
| 4931593 | rs11224789 | N.D. | | ⬚ | intron |
| 4931660 | rs10791483 | 0.478 | ✂ | ⬚ | intron |
| 4931704 | rs10791484 | N.D. | • | | intron |
| 4931821 | rs10501980 | 0.480 | ✂ | ⬚H | intron |
| 4931868 | rs10791485 | N.D. | • | ⬚ | intron |
| 4932163 | rs10791486 | N.D. | • | ⬚ | intron |
| 4932255 | rs10895124 | N.D. | | ⬚ | intron |
| 4932349 | rs11224790 | N.D. | | ⬚ | intron |
| 4932400 | rs11224791 | N.D. | | ⬚ | intron |
| 4932439 | rs11224792 | N.D. | | ⬚ | intron |
| 4932713 | rs12222976 | N.D. | | ⬚ | intron |
| 4933201 | rs11224794 | N.D. | | | intron |
| 4933214 | rs11224795 | N.D. | | | intron |
| 4933227 | rs11224796 | N.D. | | | intron |
| 4933229 | rs11224797 | N.D. | | | intron |
| 4933357 | rs11224798 | N.D. | | | intron |
| 4933361 | rs11224799 | N.D. | | | intron |
| 4933369 | rs11417954 | N.D. | | | intron |
| 4933629 | rs6590867 | N.D. | • | ⬚ | intron |
| 4933647 | rs6590868 | N.D. | • | ⬚ | intron |
| 4933862 | rs6590869 | 0.498 | ✂ | ⬚H | intron |

Fig. 11. Table 3. (Continued)

| Position | RS ID | Value | | | Region |
|---|---|---|---|---|---|
| 4933919 | rs6590870 | N.D. | | | intron |
| 4934161 | rs11224800 | N.D. | | | intron |
| 4934174 | rs11224801 | N.D. | | | intron |
| 4934344 | rs10895125 | 0.478 | | | intron |
| 4934413 | rs12804299 | N.D. | | | intron |
| 4934414 | rs12804301 | N.D. | | | intron |
| 4934657 | rs10791487 | N.D. | | | intron |
| 4934871 | rs10791488 | N.D. | | | intron |
| 4934874 | rs10597981 | N.D. | | | intron |
| 4935191 | rs7934208 | N.D. | | | intron |
| 4935213 | rs7934219 | N.D. | | | intron |
| 4935222 | rs7933359 | 0.467 | | | intron |
| 4935251 | rs10791489 | 0.468 | | | intron |
| 4935509 | rs11224802 | 0.143 | | | intron |
| 4935591 | rs10791490 | 0.468 | | | intron |
| 4935702 | rs7104033 | 0.468 | | | intron |
| 4935816 | rs10791491 | 0.468 | | | intron |
| 4935930 | rs11224805 | N.D. | | | intron |
| 4936110 | rs10656416 | N.D. | | | intron |
| 4936112 | rs10649572 | N.D. | | | intron |
| 4936140 | rs17741616 | 0.041 | | | intron |
| 4936681 | rs7105161 | 0.468 | | | intron |
| 4936692 | rs17741661 | 0.108 | | | intron |
| 4936778 | rs4477408 | N.D. | | | intron |
| 4936842 | rs4533005 | 0.468 | | | intron |
| 4936860 | rs4578354 | 0.468 | | | intron |
| 4937042 | rs4542378 | N.D. | | | intron |
| 4937965 | rs10501986 | 0.473 | | H | intron |
| 4938031 | rs10501981 | 0.474 | | H | intron |
| 4938166 | rs4262694 | 0.467 | | | intron |
| 4938438 | rs7935702 | N.D. | | | intron |
| 4938479 | rs7932871 | 0.459 | | H | intron |
| 4938682 | rs7927661 | N.D. | | | intron |
| 4938715 | rs7927674 | 0.468 | | | intron |
| 4938827 | rs7927797 | 0.471 | | | intron |
| 4938846 | rs7927803 | 0.471 | | | intron |

Fig. 11. Table 3. (Continued)

| Position | RS ID | Value | | | Region |
|---|---|---|---|---|---|
| 4938892 | rs6590871 | N.D. | | | intron |
| 4938895 | rs7928728 | N.D. | | | intron |
| 4938954 | rs6590872 | N.D. | | | intron |
| 4939065 | rs6590873 | N.D. | | | intron |
| 4939174 | rs10714032 | N.D. | | | intron |
| 4939253 | rs6590874 | 0.471 | | | intron |
| 4939900 | rs4754763 | N.D. | | | intron |
| 4940187 | rs10590147 | N.D. | | | intron |
| 4940248 | rs11224806 | N.D. | | | intron |
| 4940574 | rs10750605 | N.D. | | | intron |
| 4941352 | rs11224807 | N.D. | | | intron |
| 4942206 | rs6590875 | 0.421 | | H | intron |
| 4942237 | rs11310555 | N.D. | | | intron |
| 4942283 | rs7941212 | N.D. | | | intron |
| 4942417 | rs6590876 | N.D. | | | intron |
| 4942594 | rs6590877 | 0.434 | | | intron |
| 4942778 | rs7930876 | 0.469 | | | intron |
| 4943033 | rs7934116 | 0.473 | | | intron |
| 4943094 | rs10791492 | 0.470 | | | intron |
| 4943237 | rs10791493 | N.D. | | | intron |
| 4943333 | rs10750606 | 0.464 | | | intron |
| 4943389 | rs7109127 | 0.473 | | | intron |
| 4943856 | rs7115999 | 0.468 | | | intron |
| 4944169 | rs7113034 | N.D. | | | intron |
| 4944178 | rs7116473 | 0.477 | | | intron |
| 4944357 | rs7116629 | N.D. | | | intron |
| 4944441 | rs7127243 | 0.470 | | | intron |
| 4944525 | rs7128269 | N.D. | | | intron |
| 4945045 | rs11224808 | N.D. | | | intron |
| 4945383 | rs7925012 | 0.493 | | H | intron |
| 4945820 | rs4619120 | N.D. | | | intron |
| 4946094 | rs7927852 | 0.496 | | H | intron |
| 4946122 | rs7927859 | N.D. | | | intron |
| 4946875 | rs10895126 | 0.462 | | | intron |
| 4947028 | rs10895127 | 0.467 | | | intron |
| 4947153 | rs10895128 | N.D. | | | intron |

Fig. 11. Table 3. (Continued)

| Position | RS ID | Value | | | Region |
|---|---|---|---|---|---|
| 4947596 | rs11224810 | N.D. | | | intron |
| 4948129 | rs12277875 | N.D. | | | intron |
| 4948150 | rs11224811 | N.D. | | ▢ | intron |
| 4948442 | rs4623866 | N.D. | | ▢ | intron |
| 4948725 | rs17742220 | 0.144 | ✕ | | intron |
| 4948827 | rs6590878 | N.D. | ● | ▢ | intron |
| 4949112 | rs6590879 | 0.470 | ●✕ | ▢ | intron |
| 4949256 | rs10635008 | N.D. | | | intron |
| 4949260 | rs10689667 | N.D. | | | intron |
| 4949261 | rs10689665 | N.D. | | | intron |
| 4949345 | rs11224813 | N.D. | | | intron |
| 4949619 | rs10791494 | 0.475 | ●✕ | ▢ | intron |
| 4949937 | rs7937745 | 0.479 | ●✕ | ▢ | intron |
| 4950228 | rs4331056 | 0.473 | ●✕ | ▢ H | intron |
| 4950374 | rs4285844 | 0.475 | ●✕ | ▢ | intron |
| 4950774 | rs7123199 | 0.490 | ●✕ | ▢ | intron |
| 4950943 | rs17674687 | 0.133 | ✕ | | intron |
| 4951132 | rs10501982 | 0.234 | ●✕ | | intron |
| 4952468 | rs10675951 | N.D. | | | intron |
| 4952863 | rs12275715 | N.D. | | | intron |
| 4952887 | rs11224815 | N.D. | | ▢ | intron |
| 4953274 | rs7934774 | N.D. | ● | ▢ | intron |
| 4953627 | rs7938806 | N.D. | ● | ▢ | intron |
| 4953637 | rs12277494 | N.D. | | | intron |
| 4954255 | rs10895129 | N.D. | ● | ▢ | intron |
| 4954529 | rs7481603 | 0.311 | ●✕ | ▢ | intron |
| 4954705 | rs12279399 | N.D. | | | intron |
| 4954825 | rs11820765 | N.D. | | | intron |
| 4956818 | rs17096854 | 0.028 | ✕ | | intron |
| 4956957 | rs4272759 | 0.250 | ●✕ | ▢ H | intron |
| 4957181 | rs12786942 | N.D. | | | intron |
| 4957366 | rs10895130 | 0.489 | ●✕ | ▢ | intron |
| 4957587 | rs4271352 | N.D. | ● | ▢ | intron |
| 4957669 | rs4492783 | N.D. | | ▢ | intron |
| 4957726 | rs4481994 | N.D. | | ▢ | intron |
| 4958702 | rs11224816 | 0.488 | ●✕ | ▢ | intron |

Fig. 11. Table 3. (Continued)

| | | | | | |
|---|---|---|---|---|---|
| 4958737 | rs17096867 | 0.014 | | | intron |
| 4958774 | rs17096869 | 0.069 | ✗ | | intron |
| 4958776 | rs4754764 | N.D. | | | intron |
| 4958799 | rs12792834 | N.D. | | | intron |
| 4958921 | rs17096875 | 0.014 | | | intron |
| 4959739 | rs11224817 | N.D. | | ▯ | intron |
| 4960843 | rs12800794 | N.D. | | | intron |
| 4960866 | rs4466798 | 0.322 | ✗ | ▯H | intron |
| 4961094 | rs12801371 | N.D. | | | intron |
| 4961194 | rs11224818 | N.D. | ● | ▯ | intron |
| 4961926 | rs3924457 | 0.413 | ✗ | ▯H | intron |
| 4962968 | rs7101962 | N.D. | ● | ▯ | intron |
| 4963113 | rs7940596 | N.D. | ● | | intron |
| 4963188 | rs7926134 | N.D. | ● | ▯ | intron |
| 4963268 | rs11224819 | N.D. | | | intron |
| 4963860 | rs7106968 | 0.482 | ✗ | ▯ | intron |
| 4964495 | rs4254048 | N.D. | ● | ▯ | intron |
| 4964680 | rs11224820 | N.D. | | ▯ | intron |
| 4965902 | rs10543517 | N.D. | | | intron |
| 4966218 | rs12577149 | 0.252 | ✗ | ▯ | intron |
| 4966405 | rs12290423 | N.D. | | | intron |
| 4967061 | rs4509717 | 0.375 | ✗ | ▯H | intron |
| 4967485 | rs7119901 | N.D. | | | intron |
| 4967634 | rs7931676 | 0.191 | ✗ | ▯ | intron |
| 4968322 | rs12801997 | N.D. | | | intron |
| 4968382 | rs12294092 | N.D. | | | intron |
| 4968519 | rs7125175 | N.D. | ● | | intron |
| 4968523 | rs7113660 | N.D. | ● | | intron |
| 4968529 | rs7125178 | N.D. | ● | | intron |
| 4968552 | rs10709017 | N.D. | | | intron |
| 4969111 | rs7106085 | N.D. | ● | ▯ | intron |
| 4969399 | rs11224821 | N.D. | ● | ▯ | intron |
| 4969449 | rs12421364 | N.D. | | | intron |
| 4969554 | rs11224822 | N.D. | | | intron |
| 4969602 | rs17096881 | 0.028 | ✗ | | intron |
| 4969632 | rs7108886 | 0.496 | ✗ | ▯ | intron |

Fig. 11. Table 3. (Continued)

| | | | | | |
|---|---|---|---|---|---|
| 4970185 | rs7932074 | 0.068 | | | intron |
| 4970285 | rs10895131 | 0.143 | | | intron |
| 4970385 | rs7950828 | N.D. | | | intron |
| 4970456 | rs7933194 | N.D. | | | intron |
| 4970561 | rs11224823 | N.D. | | | intron |
| 4970722 | rs7925662 | N.D. | | | intron |
| 4970857 | rs4622224 | N.D. | | | intron |
| 4971089 | rs4360666 | 0.280 | | H | intron |
| 4971439 | rs4402260 | N.D. | | | intron |
| 4971554 | rs11224824 | 0.200 | | | intron |
| 4971847 | rs11224825 | N.D. | | | intron |
| 4971894 | rs7118839 | N.D. | | | intron |
| 4972134 | rs11224826 | N.D. | | | intron |
| 4972202 | rs4457714 | N.D. | | | intron |
| 4972271 | rs12792271 | N.D. | | | intron |
| 4972290 | rs10895132 | N.D. | | | intron |
| 4972318 | rs11224827 | 0.143 | | | intron |
| 4972369 | rs11224828 | 0.131 | | | intron |
| 4972396 | rs10895133 | 0.317 | | | intron |
| 4972578 | rs10895134 | N.D. | | | intron |
| 4972903 | rs7108296 | 0.333 | | | intron |
| 4973172 | rs7123468 | 0.290 | | | intron |
| 4973535 | rs7112388 | N.D. | | | intron |
| 4973624 | rs7112255 | 0.475 | | | intron |
| 4973758 | rs6590880 | 0.471 | | | intron |
| 4973818 | rs10791495 | N.D. | | | intron |
| 4973885 | rs6590881 | 0.464 | | | intron |
| 4973920 | rs4469857 | 0.271 | | | intron |
| 4974005 | rs4469858 | 0.385 | | | intron |
| 4974027 | rs6590882 | 0.471 | | | intron |
| 4974183 | rs4469859 | 0.468 | | | intron |
| 4974226 | rs7938237 | N.D. | | | intron |
| 4974366 | rs10895135 | 0.392 | | | intron |
| 4974391 | rs4331057 | 0.456 | | | intron |
| 4974409 | rs4331058 | N.D. | | | intron |
| 4974455 | rs4531428 | 0.355 | | H | intron |

Fig. 11. Table 3. (Continued)

| | | | | | |
|---|---|---|---|---|---|
| 4974510 | rs10643968 | N.D. | | | intron |
| 4974548 | rs4474404 | N.D. | | | intron |
| 4974578 | rs7951375 | N.D. | | | intron |
| 4974670 | rs4474405 | N.D. | | | intron |
| 4974679 | rs4462304 | N.D. | | | intron |
| 4974681 | rs11389837 | N.D. | | | intron |
| 4974709 | rs4462305 | N.D. | | | intron |
| 4974729 | rs4754012 | 0.378 | | | intron |
| 4975106 | rs17134809 | 0.371 | | | intron |
| 4975157 | rs12786923 | N.D. | | | intron |
| 4975158 | rs12786924 | N.D. | | | intron |
| 4975291 | rs11224829 | 0.398 | | | intron |
| 4975343 | rs11224830 | 0.211 | | | intron |
| 4975438 | rs7131328 | 0.290 | | | intron |
| 4975535 | rs17096904 | 0.398 | | | intron |
| 4975556 | rs10791496 | 0.448 | | | intron |
| 4975785 | rs10791497 | N.D. | | | intron |
| 4975841 | rs10895136 | N.D. | | | intron |
| 4975890 | rs10791498 | N.D. | | | intron |
| 4975944 | rs10791499 | N.D. | | | intron |
| 4975987 | rs12361104 | N.D. | | | intron |
| 4976106 | rs4754013 | N.D. | | | intron |
| 4976135 | rs11224831 | N.D. | | | intron |
| 4976344 | rs11224832 | N.D. | | | intron |
| 4976354 | rs11224833 | N.D. | | | intron |
| 4976367 | rs4754765 | N.D. | | | intron |
| 4976477 | rs11224834 | N.D. | | | intron |
| 4976501 | rs11224835 | N.D. | | | intron |
| 4976530 | rs7125321 | N.D. | | | intron |
| 4976628 | rs11224836 | N.D. | | | intron |
| 4976685 | rs12806857 | N.D. | | | intron |
| 4976744 | rs7395064 | N.D. | | | intron |
| 4976827 | rs10895137 | N.D. | | | intron |
| 4976910 | rs7125565 | N.D. | | | intron |
| 4976959 | rs12802352 | N.D. | | | intron |
| 4976962 | rs7128797 | N.D. | | | intron |

Fig. 11. Table 3. (Continued)

| | | | | | |
|---|---|---|---|---|---|
| 4977047 | rs6590883 | N.D. | | | intron |
| 4977101 | rs12800593 | N.D. | | | intron |
| 4977111 | rs6590884 | N.D. | | | intron |
| 4977153 | rs12800634 | N.D. | | | intron |
| 4977197 | rs6590885 | N.D. | | | intron |
| 4977481 | rs7109771 | N.D. | | | intron |
| 4977918 | rs12295858 | N.D. | | | intron |
| 4977942 | rs7935364 | N.D. | | | intron |
| 4978026 | rs4477410 | N.D. | | | intron |
| 4978035 | rs11224837 | N.D. | | | intron |
| 4978353 | rs10541770 | N.D. | | | intron |
| 4978371 | rs12785250 | N.D. | | | intron |
| 4978479 | rs11224838 | N.D. | | | intron |
| 4978565 | rs11224839 | N.D. | | | intron |
| 4978578 | rs11224840 | N.D. | | | intron |
| 4978642 | rs4480511 | N.D. | | | intron |
| 4978722 | rs12801413 | N.D. | | | intron |
| 4978834 | rs12803724 | N.D. | | | intron |
| 4979018 | rs4492784 | 0.485 | | H | intron |
| 4979382 | rs12288109 | N.D. | | | intron |
| 4979538 | rs12786241 | N.D. | | | intron |
| 4979652 | rs12807755 | N.D. | | | intron |
| 4979756 | rs11224841 | N.D. | | | intron |
| 4980173 | rs4486597 | N.D. | | | intron |
| 4980229 | rs7119370 | N.D. | | | intron |
| 4980673 | rs12798282 | N.D. | | | intron |
| 4980679 | rs4754767 | N.D. | | | intron |
| 4980738 | rs4754768 | N.D. | | | intron |
| 4980769 | rs4754769 | N.D. | | | intron |
| 4980785 | rs12791029 | N.D. | | | intron |
| 4980819 | rs4754014 | N.D. | | | intron |
| 4980997 | rs12793532 | N.D. | | | intron |
| 4981031 | rs4754770 | N.D. | | | intron |
| 4981261 | rs4754771 | N.D. | | | intron |
| 4981360 | rs7942189 | N.D. | | | intron |
| 4981409 | rs4754772 | N.D. | | | intron |

Fig. 11. Table 3. (Continued)

| | | | | | |
|---|---|---|---|---|---|
| 4981409 | rs10633400 | N.D. | | | intron |
| 4981486 | rs10633401 | N.D. | | | intron |
| 4981510 | rs7394770 | N.D. | * | T | intron |
| 4981615 | rs10581854 | N.D. | | | intron |
| 4981623 | rs7945348 | N.D. | | T | intron |
| 4981641 | rs4754773 | N.D. | | T | intron |
| 4981644 | rs11278881 | N.D. | | | intron |
| 4981735 | rs10895138 | N.D. | * | T | intron |
| 4981753 | rs11366849 | N.D. | | | intron |
| 4981904 | rs4754774 | 0.439 | X | TH | intron |
| 4982165 | rs5005503 | N.D. | | | intron |
| 4982173 | rs5794112 | N.D. | | | intron |
| 4982400 | rs4754775 | N.D. | | T | intron |
| 4982532 | rs10624249 | N.D. | | | intron |
| 4982787 | rs11224842 | N.D. | * | T | intron |
| 4982793 | rs12223895 | N.D. | | T | intron |
| 4983256 | rs12419234 | N.D. | | | intron |
| 4984136 | rs12222977 | N.D. | | T | intron |
| 4984191 | rs7116748 | N.D. | * | T | intron |
| 4984194 | rs11224843 | N.D. | | T | intron |
| 4984942 | rs7929416 | N.D. | * | | intron |
| 4985301 | rs7943559 | N.D. | * | | intron |
| 4985446 | rs12362645 | N.D. | | T | intron |
| 4986033 | rs10791500 | N.D. | * | T | intron |
| 4986193 | rs6590886 | N.D. | * | T | intron |
| 4986262 | rs12282925 | N.D. | | | intron |
| 4986519 | rs11224845 | N.D. | | T | intron |
| 4986612 | rs12807277 | N.D. | | T | intron |
| 4986613 | rs4301757 | N.D. | | T | intron |
| 4986632 | rs11224846 | N.D. | | T | intron |
| 4986700 | rs4597037 | N.D. | * | | intron |
| 4986897 | rs7115426 | N.D. | * | | intron |
| 4986992 | rs4754776 | N.D. | * | T | intron |
| 4987172 | rs4237602 | 0.325 | *X | T | intron |
| 4987317 | rs11224847 | N.D. | | T | intron |
| 4987358 | rs4237603 | 0.422 | *X | TH | intron |

Fig. 11. Table 3. (Continued)

| | | | | | |
|---|---|---|---|---|---|
| 4987522 | rs11224849 | N.D. | | ☐ | intron |
| 4987567 | rs5794113 | N.D. | | | intron |
| 4987654 | rs11224850 | N.D. | | ☐ | intron |
| 4987726 | rs12577264 | N.D. | | | intron |
| 4987788 | rs11224851 | N.D. | | ☐ | intron |
| 4987796 | rs11224852 | N.D. | | | intron |
| 4987842 | rs12363799 | N.D. | | ☐ | intron |
| 4988209 | rs12798819 | N.D. | | | intron |
| 4988291 | rs9888232 | N.D. | | | intron |
| 4988347 | rs7926503 | N.D. | ☐ | ☐ | intron |
| 4988939 | rs12278493 | N.D. | | | intron |
| 4988955 | rs11224853 | N.D. | | | intron |
| 4989147 | rs7927579 | N.D. | ☐ | ☐ | intron |
| 4990187 | rs7119712 | N.D. | | | intron |
| 4990744 | rs12280648 | N.D. | | | intron |
| 4990778 | rs7932069 | N.D. | ☐ | ☐ | intron |
| 4991365 | rs7935659 | N.D. | | | intron |
| 4991397 | rs7935759 | N.D. | | | intron |
| 4991525 | rs7935886 | N.D. | | | intron |
| 4991538 | rs12802697 | N.D. | | | intron |
| 4991547 | rs12802004 | N.D. | | | intron |
| 4991564 | rs12807412 | N.D. | | | intron |
| 4991846 | rs11224854 | N.D. | | | intron |
| 4992235 | rs11224855 | N.D. | | | intron |
| 4992456 | rs4754777 | 0.323 | ☐ | ☐ | intron |
| 4992667 | rs11358235 | N.D. | | | intron |
| 4992783 | rs11358236 | N.D. | | | intron |
| 4992791 | rs11286449 | N.D. | | | intron |
| 4992854 | rs6590887 | N.D. | ☐ | | intron |
| 4992888 | rs7940203 | N.D. | ☐ | ☐ | intron |
| 4992925 | rs12796089 | N.D. | | | intron |
| 4992931 | rs12790232 | N.D. | | | intron |
| 4992932 | rs12796092 | N.D. | | | intron |
| 4992998 | rs12796313 | N.D. | | | intron |
| 4993103 | rs12796526 | N.D. | | | intron |
| 4993145 | rs12796563 | N.D. | | | intron |

Fig. 11. Table 3. (Continued)

| | | | | | |
|---|---|---|---|---|---|
| 4993162 | rs12796567 | N.D. | | | intron |
| 4993195 | rs12796758 | N.D. | | | intron |
| 4993243 | rs12789435 | N.D. | | | intron |
| 4993245 | rs12796783 | N.D. | | | intron |
| 4993256 | rs12796792 | N.D. | | | intron |
| 4993267 | rs12796962 | N.D. | | | intron |
| 4993292 | rs12796974 | N.D. | | | intron |
| 4993306 | rs12791703 | N.D. | | | intron |
| 4993538 | rs10219300 | N.D. | | ꭤ | intron |
| 4993742 | rs10791501 | N.D. | | | intron |
| 4994156 | rs10219398 | 0.213 | ✗ | H | intron |
| 4994302 | rs12226165 | N.D. | | | intron |
| 4994518 | rs12799086 | N.D. | | | intron |
| 4994524 | rs11224856 | N.D. | | | intron |
| 4994526 | rs10791502 | N.D. | | | intron |
| 4994990 | rs12281465 | N.D. | | ꭤ | intron |
| 4995131 | rs5794114 | N.D. | | | intron |
| 4995153 | rs5794115 | N.D. | | | intron |
| 4995241 | rs4281451 | N.D. | | | intron |
| 4995247 | rs4501953 | N.D. | | ꭤ | intron |
| 4995262 | rs10895139 | N.D. | | ꭤ | intron |
| 4995264 | rs12364903 | N.D. | | ꭤ | intron |
| 4995532 | rs11356689 | N.D. | | | intron |
| 4995577 | rs9326314 | N.D. | ● | ꭤ | intron |
| 4995661 | rs11224857 | N.D. | | ꭤ | intron |
| 4995688 | rs7937329 | N.D. | | H | intron |
| 4995769 | rs7936514 | 0.491 | ✗ | H | intron |
| 4995832 | rs7926874 | N.D. | | | intron |
| 4995867 | rs7952182 | 0.010 | ✗ | H | intron |
| 4996288 | rs11224858 | N.D. | | | intron |
| 4996293 | rs7116242 | N.D. | | | intron |
| 4996395 | rs7115437 | N.D. | | ꭤ | intron |
| 4996535 | rs7115586 | N.D. | | | intron |
| 4996584 | rs4503499 | N.D. | ● | ꭤ | intron |
| 4996876 | rs11224859 | N.D. | | | intron |
| 4997357 | rs11224860 | N.D. | | | intron |

Fig. 11. Table 3. (Continued)

| | | | | | |
|---|---|---|---|---|---|
| 4997971 | rs7123327 | N.D. | ● | ● | intron |
| 4997977 | rs7112841 | N.D. | | | intron |
| 4998104 | rs11224862 | N.D. | | ● | intron |
| 4998489 | rs4754778 | N.D. | ● | ● | intron |
| 4998714 | rs11606855 | N.D. | | | intron |
| 4998977 | rs10791503 | N.D. | ● | ● | intron |
| 4999033 | rs12291854 | N.D. | | | intron |
| 4999105 | rs10791504 | N.D. | ● | ● | intron |
| 4999137 | rs10895140 | N.D. | | ● | intron |
| 4999157 | rs10895141 | N.D. | | ● | intron |
| 4999205 | rs12796392 | N.D. | | | intron |
| 4999298 | rs10895142 | N.D. | ● | ● | intron |
| 4999413 | rs4754779 | N.D. | | ● | intron |
| 4999780 | rs7932338 | N.D. | ● | ● | intron |
| 4999831 | rs6590888 | N.D. | ● | ● | Intron |
| 5000230 | rs12803198 | N.D. | | | intron |
| 5000394 | rs7110783 | N.D. | | ● | intron |
| 5000402 | rs12801488 | N.D. | | | intron |
| 5000607 | rs6590889 | N.D. | ● | ● | intron |
| 5000915 | rs11603969 | N.D. | | | intron |
| 5001905 | rs11606771 | N.D. | ● | ● | intron |
| 5002040 | rs11606784 | N.D. | ● | ● | intron |
| 5002397 | rs12793021 | N.D. | | | intron |
| 5002646 | rs11224865 | N.D. | ● | ● | intron |
| 5002880 | rs12146595 | N.D. | | ● | intron |
| 5002885 | rs11224866 | N.D. | ● | ● | intron |
| 5003098 | rs12366002 | N.D. | | | intron |
| 5003195 | rs7482684 | N.D. | | | Intron |
| 5003465 | rs7480622 | N.D. | ● | ● | intron |
| 5003540 | rs7482758 | N.D. | ● | ● | intron |
| 5003770 | rs12366048 | N.D. | | ● | intron |
| 5004006 | rs11224867 | N.D. | ● | ● | intron |
| 5004101 | rs12787200 | N.D. | | | intron |
| 5004673 | rs7952280 | N.D. | ● | ● | intron |
| 5004804 | rs7951517 | N.D. | ● | ● | intron |
| 5004815 | rs7481496 | N.D. | ● | ● | intron |

Fig. 11. Table 3. (Continued)

| | | | | | | |
|---|---|---|---|---|---|---|
| 5005119 | rs7938938 | N.D. | ● | ⊔ | | intron |
| 5005166 | rs11224868 | N.D. | | | | intron |
| 5005250 | rs11224869 | N.D. | | ⊔ | | intron |
| 5005329 | rs11224870 | N.D. | | ⊔ | | intron |
| 5005556 | rs12361061 | N.D. | | | | intron |
| 5005627 | rs11224871 | N.D. | | | | intron |
| 5005883 | rs11224872 | N.D. | | ⊔ | | intron |
| 5006328 | rs4754015 | N.D. | ● | | | intron |
| 5006408 | rs11493972 | N.D. | | | | intron |
| 5006695 | rs7128403 | 0.041 | ●✕ | | | intron |
| 5006948 | rs11224873 | N.D. | | | | intron |
| 5007105 | rs11224874 | N.D. | | | | intron |
| 5007199 | rs10895144 | N.D. | | ⊔ | | intron |
| 5007206 | rs10895145 | N.D. | | ⊔ | | intron |
| 5007221 | rs10895146 | N.D. | | ⊔ | | intron |
| 5007394 | rs11224875 | N.D. | | | | intron |
| 5007422 | rs11224876 | N.D. | | | | intron |
| 5007568 | rs11224877 | N.D. | ● | ⊔ | | intron |
| 5007605 | rs7129301 | N.D. | | | | intron |
| 5008070 | rs4604837 | N.D. | | | | intron |
| 5008122 | rs7129904 | 0.405 | ●✕ | ⊔ | | intron |
| 5008224 | rs7113536 | 0.492 | ●✕ | ⊔ | | intron |
| 5008329 | rs4353244 | N.D. | ● | ⊔ | | intron |
| 5008332 | rs12222757 | N.D. | | | | intron |
| 5008675 | rs4408275 | N.D. | ● | ⊔ | | intron |
| 5008688 | rs4406798 | N.D. | | ⊔ | | intron |
| 5009007 | rs10501985 | 0.480 | ●✕ | | H | intron |
| 5009188 | rs11224878 | 0.332 | ●✕ | | | intron |
| 5009717 | rs17096917 | 0.081 | ✕ | | | intron |
| 5010213 | rs4394815 | 0.389 | ✕ | ⊔H | | intron |
| 5010584 | rs10791506 | N.D. | ● | | | intron |
| 5011037 | rs11224879 | N.D. | | | | intron |
| 5011080 | rs7103450 | N.D. | ● | ⊔ | | intron |
| 5011392 | rs11280199 | N.D. | | | | intron |
| 5011774 | rs4326755 | N.D. | | ⊔ | | intron |
| 5012119 | rs7479835 | N.D. | ● | ⊔ | | intron |

Fig. 11. Table 3. (Continued)

| | | | | | | | |
|---|---|---|---|---|---|---|---|
| 5012280 rs10895147 | 0.405 | | | intron | | | |
| 5012332 rs10895148 | N.D. | | | intron | | | |
| 5012338 rs12275413 | N.D. | | | intron | | | |
| 5013034 rs11224880 | N.D. | | | intron | | | |
| 5013043 rs11224881 | N.D. | | | intron | | | |
| 5013197 rs4754780 | N.D. | | | intron | | | |
| 5013328 rs7935407 | N.D. | | | intron | | | |
| 5013748 rs10551448 | N.D. | | | intron | | | |
| 5014181 rs11224882 | N.D. | | | intron | | | |
| 5014609 rs7120953 | 0.428 | | | intron | | | |
| 5014747 rs7121108 | N.D. | | | intron | | | |
| 5014924 rs4754781 | N.D. | | | intron | | | |
| 5015334 rs4754782 | N.D. | | | intron | | | |
| 5015720 rs10712341 | N.D. | | | intron | | | |
| 5015722 rs11341799 | N.D. | | | intron | | | |
| 5015872 rs17675774 | 0.262 | | | intron | | | |
| 5016051 rs11224883 | N.D. | | | intron | | | |
| 5016411 rs17096918 | 0.371 | | | intron | | | |
| 5016608 rs3802829 | N.D. | | | nonsynonymous T | Ser [S] | 1 | 15 |
| | N.D. | | | contig reference C | Pro [P] | 1 | 15 |
| 5016904 rs3824934 | N.D. | | | untranslated | | | |
| 5017074 rs17096920 | 0.014 | | | untranslated | | | |

TRPC6 INVOLVED IN GLOMERULONEPHRITIS

RELATED APPLICATIONS

This application is a continuation of U.S. patent application Ser. No. 12/782,075, filed May 18, 2010, now U.S. Pat. No. 9,433,642, which is a continuation of U.S. patent application Ser. No. 11/716,050, filed Mar. 9, 2007, now U.S. Pat. No. 7,745,597, which is a divisional of U.S. patent application Ser. No. 11/417,113, filed May 4, 2006, now abandoned, which claims priority from U.S. Provisional Patent Application No. 60/677,825, filed May 5, 2005. The entire contents of these applications are incorporated herein by reference in their entirety.

GOVERNMENT SUPPORT

The invention of the present application was made using funds from the U.S. government. The U.S. government may therefore retain certain rights under the terms of grant 5K08-DK02815-04.

TECHNICAL FIELD OF THE INVENTION

This invention is related to the area of kidney disease. In particular, it relates to diagnosis and treatment and drug discovery for kidney disease.

BACKGROUND OF THE INVENTION

FSGS is a significant cause of end-stage renal disease world-wide and up to one-fifth of dialysis patients have this diagnosis (1, 2). The prevalence of FSGS is increasing yearly and the incidence is particularly high in the black population (1, 3). FSGS is a pathological entity in which the glomerulus is primarily targeted. Typical manifestations of FSGS include proteinuria, hypertension, renal insufficiency and eventual kidney failure. Our understanding of the pathogenesis of FSGS is incomplete and there are no consistently effective treatments.

Analysis of disease-causing mutations in hereditary FSGS and congenital nephrotic syndromes has provided striking new insights into the pathogenesis of nephrotic syndrome. The previous identification of at least three genes causing familial FSGS and hereditary nephrotic syndromes underscores the significant genetic heterogeneity in this disorder (4-6). These studies have highlighted the importance of abnormalities in the podocyte and the slit diaphragm of the glomerulus to the development of the severe proteinuria that characterizes the nephrotic syndrome.

Previously, we ascertained and characterized a large New Zealand family of British origin with autosomal dominant hereditary FSGS (FIG. 4) (7). The character of the disease in this family is particularly aggressive. Affected individuals typically present with high-grade proteinuria in their $3^{rd}$ or $4^{th}$ decade and approximately 60% progress to end-stage renal disease (ESRD). The average time between initial presentation and the development of ESRD is 10 years. A genomic screen performed on this kindred localized the disease-causing mutation to chromosome 11q (8). However, this genomic region is very large and contains hundreds of genes.

There is a continuing need in the art to identify genes and proteins which are associated with or causative of kidney disease, so that they can be used to more accurately and effectively diagnose and treat kidney disease.

SUMMARY OF THE INVENTION

The present invention has many aspects. A first aspect of the invention is a cell-free preparation of a mutant TRPC6 protein comprising a glutamine at residue 112 of TRPC6.

Another aspect of the invention is a cell-free preparation of a polypeptide comprising at least six contiguous amino acid residues of a P112Q mutant of TRPC6, wherein the polypeptide comprises residue 112.

An additional aspect of the invention is a cell-free preparation of a polynucleotide which encodes a human TRPC6 polypeptide of at least six contiguous amino acid residues, said polypeptide comprising a P112Q substitution.

In one embodiment of the invention a cell culture comprising a human cell is provided. The human cell comprises a polynucleotide which encodes a human TRPC6 protein comprising a P112Q substitution.

According to another aspect of the invention a cell-free preparation of an antisense polynucleotide is provided. The polynucleotide comprises at least 18 contiguous nucleotides which are complementary to a human TRPC6 coding sequence selected from the group consisting of wild-type and a P112Q mutant.

An additional embodiment of the invention provides a method of inhibiting TRPC6 channels in a kidney of a glomerulonephritis patient. An inhibitor of TRPC6 channels is administered to the patient. Calcium ion influx is thereby reduced.

Yet another embodiment of the invention provides a method of inhibiting expression of TRPC6 channels in the kidney of a glomerulonephritis patient. An antisense polynucleotide is administered to a kidney of the patient. Expression of TRPC6 channels is thereby inhibited. The antisense polynucleotide comprises at least 18 contiguous nucleotides which are complementary to a human TRPC6 coding sequence selected from the group consisting of wild-type and a P112Q mutant.

Still another aspect of the invention is a method of identifying a subject at increased risk of developing Focal and Segmental Glomerulosclerosis (FSGS). A sequence feature of a TRPC6 gene in a subject is determined. The determined sequence feature of the gene of the subject is compared to the sequence feature in a reference wild-type TPRC6 gene. The subject is identified as being at increased risk of developing FSGS if the sequence feature of the gene of the subject differs from the reference or if it matches a mutation associated with FSGS.

Another embodiment of the invention provides another method of identifying a person at increased risk of developing Focal and Segmental Glomerulosclerosis (FSGS). A sequence feature of a TRPC6 protein in a subject is determined. The determined sequence feature of the protein of the subject is compared to the sequence feature in a reference wild-type TPRC6 protein. The subject is identified as being at increased risk of developing FSGS if the sequence feature of the protein of the subject differs from the reference or if it matches a mutation associated with FSGS.

Another embodiment of the invention is a container comprising a set of primer pairs for amplifying all or part of TRPC6 sequences. The set comprises a pair which amplifies all or part of exon 2 sequences of TRPC6.

Still another aspect of the invention is a probe for detecting a C335A mutation. The probe comprises a single stranded or double stranded polynucleotide of at least 15 nucleotides which are complementary to a contiguous portion of a human TRPC6 gene which comprises nucleotide 335 of the coding sequence.

According to another embodiment of the invention a cell-free preparation of an antibody is provided. The antibody preferentially binds to a TRPC6 protein with a P112Q substitution relative to a TRPC6 protein with a proline at residue 112.

Another aspect of the invention is embodied by a method of screening for candidate agents useful for treating FSGS. A wild-type or mutant form of TRPC6 protein is contacted with a test substance. Activity of the form of TRPC6 protein is measured. A test substance is identified as a candidate agent for treating FSGS if it inhibits activity of the TRPC6 protein.

Another aspect of the invention is embodied by a method of screening for candidate agents useful for treating glomerulonephritis. A wild-type or mutant form of TRPC6 protein is contacted with a test substance. Activity of the form of TRPC6 protein is measured. A test substance is identified as a candidate agent for treating glomerulonephritis if it inhibits activity of the TRPC6 protein.

An additional embodiment of the invention is a method of classifying a patient with Focal and Segmental Glomerulosclerosis (FSGS). A sequence feature of a TRPC6 gene in a subject with FSGS is determined. The determined sequence feature of the gene of the subject is compared to the sequence feature in a reference wild-type TPRC6 gene. The subject is identified as having a TRPC6 mutation if the sequence feature of the gene of the subject differs from the sequence feature in the reference or if it matches a mutation associated with FSGS.

Still another embodiment of the invention is a method of classifying a patient with Focal and Segmental Glomerulosclerosis (FSGS). A sequence feature of a TRPC6 protein in a subject with FSGS is determined. The determined sequence feature of the gene of the subject is compared to the sequence feature in a reference wild-type TPRC6 protein. The subject is identified as having a TRPC6 mutation if the sequence feature of the protein of the subject differs from the sequence feature in the reference or if it matches a mutation associated with FSGS.

These and other embodiments which will be apparent to those of skill in the art upon reading the specification provide the art with reagents and methods for detection, diagnosis, therapy, prognosis, and drug screening pertaining to glomerulonephritis and FSGS.

BRIEF DESCRIPTION OF THE DRAWINGS

FIGS. 1A-1B. (FIG. 1. A) Minimal candidate region (MCR) of FSGS on human chromosome 11q. The area of interest is flanked by markers D11S1876 and D11S1339. The genetic distance from the centromere (cent) was obtained from the website at UCSC Genome Browser: ucsc.edu. Black squares indicate common alleles among affected individuals. Light squares indicate recombination. Individual 165 is the parent of individual 9044. Individual 9014 provides an example of the ancestral affected haplotype. All individuals represented are affected. The MCR is defined by individual 9044. Microsatellite markers in bold indicate original flanking markers. Gray box indicates candidate gene region. tel=telomere. (FIG. 1. B) Sequence chromatogram of exon 2 of TRPC6. The arrows highlight the C/A mutation.

(FIG. 2A) Immunofluorescent staining of normal human renal cortical tissue with rabbit antibody against human TRPC6. In this representative photomicrograph, specific staining within a glomerulus (G) and the epithelium of surrounding tubules (T) is easily seen. (FIG. 2B) Negative control of an adjacent section also stained with the primary anti-TRPC6 antibody in the presence of the immunizing peptide. There is minimal non-specific staining. Bars in panels A and B=25 Fluorescent in situ hybridization (FISH) of TRPC6 mRNA in normal human renal cortex. (FIG. 2C) TRPC6 antisense probe generated from nucleotides 2301-3621 from TRPC6 mRNA [Accession number AJ006276]. (FIG. 2D) Hybridization with the corresponding TRPC6 sense probe. Scale bar=90 microns. (FIG. 2E) and (FIG. 2F) High power photomicrographs of the same sense and antisense probes. Scale bar=40 microns. Widespread expression of TRPC6 mRNA was detected throughout the kidney in both glomeruli and tubular epithelia. Background staining in panels D and F reflects autofluorescence from red blood cells trapped at the time of kidney harvest. Arrows highlight glomeruli. Asterisks are centered in renal tubules.

(FIG. 3A) Intracellular calcium concentrations were measured after OAG perfusion. TRPC6$^{P112Q}$ transfected cells had significantly higher calcium concentrations than cells transfected with WT TRPC6. The peak influx $[Ca^{2+}]i$ is depicted in the bar graph below the tracing. (FIG. 3B) Angiotensin-II induced intracellular calcium concentrations were measured. The peak influx $[Ca^{2+}]i$ is depicted in the bar graph below the tracing. Again, TRPC6$^{P112Q}$ transfected cells had significantly higher calcium concentrations than cells transfected with WT TRPC6. Each trace represents the mean value derived from 15-20 cells in a single experiment, each experiment was replicated three times, with similar results. The error bars represent standard deviation. (FIG. 3C) Whole cell current recordings of HEK 293 cells expressing either WT TRPC6 or TRPC6$^{P112Q}$ protein. Considerable inward currents in normal Na$^+$ extracellular solution were observed in WT TRPC6 cells. However, inward currents were significantly larger in TRPC6$^{P112Q}$ cells. When cells were perfused with 100 μM UTP, even larger inward currents were obtained. Cells expressing TRPC6$^{P112Q}$ mutation conducted 2-3 times more current than the WT TRPC6 expressing cells as depicted in the bar graph next to the current recordings. (FIG. 3D) Surface expression experiments in HEK 293 cells transfected with TRPC6 protein. Biotinylation was used to quantitate cell surface expression of TRPC6 proteins. Cells expressing TRPC6-V5 or TRPC6$^{P112Q}$-V5 were incubated with biotin-SS reagent followed by pull-down with streptaviden agarose beads. Immunoblotting with an anti-V5 antibody of surface and whole cell lysates demonstrate increased surface expression of the TRPC6$^{P112Q}$ compared to wild-type TRPC6 protein. Immunoblotting with an anti-transferrin receptor antibody (TfR) is located in the middle row and shows no difference in the surface expression of the constitutively active plasma membrane receptor (95 kD band). Each experiment was replicated four times, with similar results. Densitometry measurement in relative units are depicted in the bar graph next to the immunoblot (the results from all four replicants are quantitated). The error bars represent standard error.

Definition of Disease Status:

Affected—Family members who had a renal biopsy demonstrating FSGS without evidence of other systemic diseases that have been known to cause FSGS, were on dialysis or had undergone renal transplantation.

Probably affected—Greater than or equal to 3+-4+proteinuria by qualitative urinalysis, in the absence of other systemic diseases likely to lead to proteinuria.

Unknown—Less than 1-2+proteinuria or 500 mg of proteinuria on 24-hour urine collection.

Unaffected—If they had no detectable proteinuria on qualitative urinalysis or were unrelated married-in spouses.

FIG. 5. Proline 112 is highly conserved in evolution and is present in TRPC protein homologs from *Mus musculus*, *Rattus norvegicus*, *Drosophila melanogaster*, *Caenorhabditis elegans* and *Cavia porcellus* (SEQ ID NOS: 1-6). The arrow indicates the mutated proline. Comparative alignments with the mouse, human and rat sequences indicate that a homolog of the TRPC protein family is also present in zebrafish (*Danio rerio*) and pufferfish (*Fugu rubripes*) and that this proline is also conserved in these organisms (see the world wide web site at ensembl.org). Within the TRPC family, TRPC3, −6 and −7 all contain the conserved proline. TRPC4 and −5 have an alanine at this position, which, like proline, is a non-polar amino acid, while TRPC1 has a tyrosine at this position. TRPC2 is a pseudogene in humans. Genebank Accession Numbers: TRPC6 *Homo sapiens*, N_004612; *Mus musculus*, Q61143; *Rattus norvegicus*, N_446011; *Caenorhabditis elegans*, N_498881; *Drosophila Melanogaster*, N_476895; *Cavia porcellus*, CAC06051.

Figure 6:
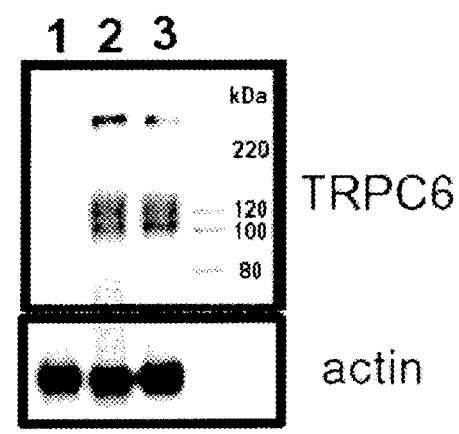

FIG. 6. Western blot of protein extracts from HEK 293 cells transfected with empty vector (lane 1), TRPC6$^{P112Q}$ (lane 2) or TRPC6 (lane3). Blots were incubated with specific antibodies against TRPC6 and actin. The immunoblot reveals three different bands and while there are different isoforms of TRPC6, there is evidence that this is glycosylation as TRPC6 is known to be heavily glycosylated (8).

Figure 7:
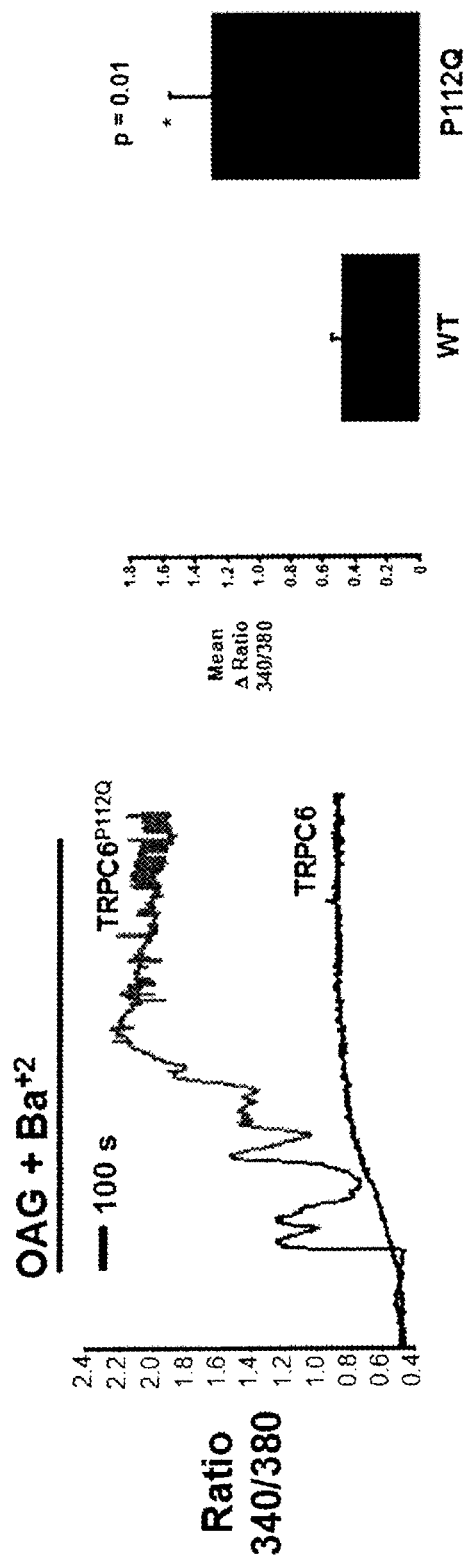

FIG. 7. OAG-stimulated barium transients were measured using the Fura-2 method in HEK293 cells transfected with WT TRPC6 (blue) or TRPC6P112Q (red). Fura fluorescence shifts in a similar pattern with barium and calcium, barium was used as a surrogate for calcium in these assays (9). As expected, OAG perfusion increased late barium transients in cells transfected with WT TRPC6. In contrast, barium influx was significantly enhanced in TRPC6P112Q-expressing cells exposed to OAG, reflecting dramatic exaggeration of intracellular cation concentration in cells expressing the mutant protein (Δ340/380 ratio TRPC6P112Q=1.30±0.7 vs. WT TRPC6=0.49±0.18; p=0.01). There are fluctuations of barium entry in the HEK 293 cells with the mutant construct. We postulate that this mutation causes disordered and dysregulated calcium entry. Y-axis is wavelength. The mean change in fluorescence is depicted by the bar graph. Error bars represent standard deviation.

Figure 8:
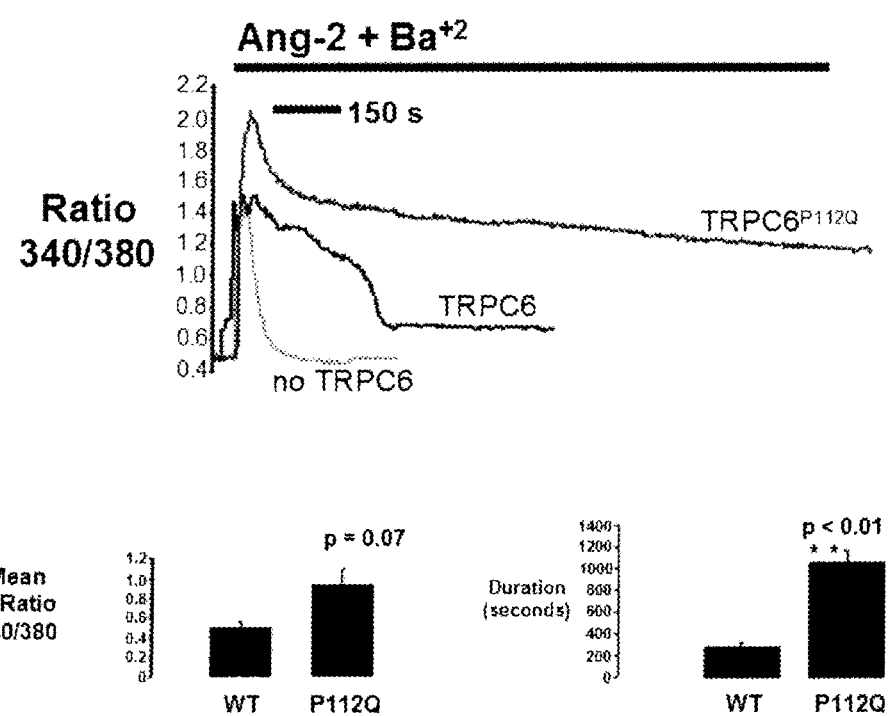

FIG. 8. Angiotensin II-induced barium transients were measured in HEK 293 cells transfected with AT1 receptor alone (green) or co-transfected with the AT1 receptor along with wild-type TRPC6 (blue) or TRPC6$^{P112Q}$ (red). Upon exposure to angiotensin II, large barium transients were triggered in both WT- and TRPC6$^{P112Q}$-transfected cells and the amplitude of the initial barium signal tended to be higher in the TRPC6$^{P112Q}$ cells. The Y-axis is wavelength. Moreover, the duration of the signal was prolonged in the TRPC6$^{P112Q}$ cells (1054±282 seconds) compared with cells transfected with WT TRPC6 (271±121 seconds; p <0.01). The duration and amplitude are depicted in the bar graph below the tracing. Error bars represent standard deviation.

FIG. 9. Table 1 showing primer sequences for TRPC6 (SEQ ID NO: 7-62).

FIG. 10. Table 2 showing SNPs in mRNA.

FIG. 11. Table 3 showing SNPs in gene.

DETAILED DESCRIPTION OF THE INVENTION

We have identified TRPC6 as a disease-gene causing hereditary FSGS. Because ion channels such as TRPC6 tend to be amenable to pharmacological manipulation, TRPC6 is identified as a useful therapeutic target in chronic kidney disease, including glomerulonephritis. Glomerulonephritis may be associated with any of the following conditions, without limitation: Focal Segmental Glomerulosclerosis (FSG), Goodpasture's syndrome, an IgA nephropathy, IgM mesangial proliferative glomerulonephritis, Lupus nephritis, Membranoproliferative glomerulonephritis I, Membranoproliferative glomerulonephritis II, Membranoproliferative glomerulonephritis III, post-streptococcal glomerulonephritis, rapidly progressive (crescentic) glomerulonephritis, membranous nephropathy, and diabetic nephropathy.

A cell-free preparation according to the present invention may comprise either polynucleotide or protein. Typically, the polynucleotide or protein will be extracted from the cells by breaking the cell membrane and optionally removing non-desired components. For example, proteins or nucleic acids can be removed if not desired using enzymatic degradation. Alternatively, desired proteins or nucleic acids can be purified using sequence-specific reagents, including but not limited to oligonucleotide probes, primers, and antibodies. Lysozyme and/or detergents and/or pressure can be used to break cells, for example. Techniques for isolating cell-free preparations are well known in the art, and any that are convenient can be used.

The P112Q mutant TRPC6 protein of the invention has a glutamine at residue 112 in place of the proline which is found in normal, non-affected humans. See SEQ ID NO: 63 to determine which residue is residue 112. See also SEQ ID NO: 65 which contains a P15S single nucleotide polymorphism at residue 15. Both of these are considered to be wild-type with respect to FSGS. Additional polymorphisms which do not affect calcium ion channel function, as described herein, may be present in addition to the P112Q substitution mutation. With respect to the TRPC6 gene, over 600 SNPs are known which do not affect the encoded protein. These include two synonymous SNPs at codons 904 and 561, as well as numerous SNPs in untranslated regions and in introns. See Tables 2 and 3. These, too, are considered wild-type with respect to FSGS.

Sequence features, according to the present invention, can be determined using any techniques which detect directly or indirectly a change in a protein or nucleic acid sequence. Thus, for example, if a mutation causes premature truncation, such a sequence feature can be detected by determining the size of the encoded mRNA or protein. Directly determining amino acid or nucleotide sequences can be used, and these techniques are well known in the art. Antibodies that are specific for a sequence feature can be used for probing mutant proteins. Probes and or primers that hybridize to wild-type or a particular mutation can be used. Any technique which detects such hybridization or the lack thereof can be used without limitation.

Polypeptides according to the present invention which contain residue 112 of TRPC6 protein can be used inter alia for raising antibodies. Such polypeptides are typically less than full-length, 931 residue proteins. Preferably such residues are at least 6, 7, 8, 9, 10, 11, 12, 13, 14, 15, 17, 19, 21, 23, or 25 residues in length. As an example, if the polypeptide is 6 residues in length, than it can comprises residues 112-117, 111-116, 110-115, 109-114, 108-113, or 107-112. Sufficient residues are desired to form a good immunogen or blocking antigen for use in assays. It may be desirable to conjugate or genetically fuse additional sequences to the polypeptide, for example, to boost immunogenicity, to enhance purification, to facilitate production or expression, or to facilitate detection. Any sequences as are convenient may be used for these or other purposes. The size of these additional sequences may vary greatly, but typically will be at least 2, 4, 6, or 8 amino acid residues in length. The polypeptide may contain either proline (wild-type) or glutamine (mutant) residue at position 112.

While particular nucleotide sequences which are found in humans are disclosed herein (see, e.g., SEQ ID NO: 64 and the SNPs shown in Tables 2 and 3) any nucleotide sequences may be used which encode a desired form of TRPC6. Thus non-naturally occurring sequences may be used. These may be desirable, for example, to enhance expression in heterologous expression systems of polypeptides or proteins of TRPC6. Computer programs for generating degenerate coding sequences are available and can be used for this purpose. Pencil, paper, the genetic code, and a human hand can also be used to generate degenerate coding sequences. For production purposes, it may be desirable to genetically engineer a coding sequence of a TRPC6 protein or polypeptide into an expression vector. Such vectors will typically contain an origin of replication, either of viral or plasmid origin. Such polynucleotides and/or vectors can be replicated and/or expressed in cell culture. Preferably the cultures will be of mammalian cells, and more preferably of human cells. However, other cell types may be advantageous for production, including but not limited to yeast cells, insect cells, and avian cells.

Antisense constructs, antisense oligonucleotides, RNA interference constructs or siRNA duplex RNA molecules can be used to interfere with expression of TRPC6. Typically at least 15, 17, 18, 19, or 21 nucleotides of the complement of TRPC6 mRNA sequence are sufficient for an antisense molecule. Typically at least 18, 19, 21, 22, or 23 nucleotides of TRPC6 are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired TRPC6 sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester WC, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

Antisense or RNA interference molecules can be delivered in vitro to cells or in vivo, e.g., to tumors of a mammal. Typical delivery means known in the art can be used. For example, delivery to a diseased kidney can be accomplished by direct intrarenal injections. Other modes of delivery can be used without limitation, including: intravenous, intramuscular, intraperitoneal, intraarterial, local delivery during surgery, endoscopic, subcutaneous, and per os. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

Because the channel activity of the disease-associated variant appears to cause increased calcium channel activity, inhibitors of such channel activity can be used therapeutically. Any inhibitor known in the art can be used, including but not limited to 2-aminoethoxy diphenyl borate, gadolinium, and SKF96365. Such inhibitors may have a therapeutic benefit in glomerulonephritis, whether or not the patient carries the P112Q variant. Thus a patient with any glomerulonephritis may be treated with inhibitor. Such patients include those with Focal Segmental Glomerulosclerosis (FSG), Goodpasture's syndrome, an IgA nephropathy, IgM mesangial proliferative glomerulonephritis, Lupus nephritis, Membranoproliferative glomerulonephritis I, Membranoproliferative glomerulonephritis II, Membranoproliferative glomerulonephritis III, post-streptococcal glomerulonephritis, rapidly progressive (crescentic) glomerulonephritis, membranous nephropathy, and diabetic nephropathy.

Additional calcium channel activity inhibitors can be screened using assays described in the examples below. Cells transfected with a coding sequence for the P112Q variant or cells transfected with a coding sequence for the wild-type TRPC6 can be used as test cells. Ion currents or intracellular calcium accumulation can be measured. The effects of various test substances on the ion currents or intracellular calcium accumulation can be determined and inhibitors thereby identified. Inhibitors are candidate therapuetic agents for treating glomerulonephritis.

Because FSGS associated with the TRPC6 mutation first manifests itself in adults, the identification of a mutation in TRPC6 can be used to predict which children or young adults are likely to manifest the disease. This is especially true among family members of affected individuals. Similarly, identifying family members who do not carry a mutation can also be useful so that anxiety and monitoring and preventive steps can be diminished. Any altered sequence in the TRPC6 gene or protein relative to normal unaffected controls will suggest an increased risk. Further functional tests of the mutant protein may be used to confirm a phenotype of any new mutations identified. Disease causing mutations will cause channel activity similar to that of the P112Q mutation, i.e., increased calcium ion influx into cells. A mutation can be detected either at the nucleic acid or at the protein level. As indicated above, synonymous mutations are unlikely to cause any changed phenotype associated with disease.

Primer pairs are provided in a single divided or undivided container. Each primer may be packaged separately or in pairs. Similarly, each pair may be packaged separately or in sets. Primers are useful for amplifying regions of TRPC6, especially exon 2, so that mutations can be identified in test samples. Preferably the primers include a pair which amplifies a segment containing codon 112 of TRPC6. Primers can be allele specific, e.g., they will amplify only in the presence of a specific allele, or they may amplify more than one allelic form. An allele-specific primer might hybridize, e.g., to a nucleotide at position 335, either a Cytosine or an Adenine. Probes similarly can be allele specific or not. Probes typically contain a readily detectable moiety, such as a fluorescent, bioluminescent, enzymatic, or radioactive moiety. Probes and primers are typically at least 12, 14, 16, 18, 20, 22, or 25 nucleotides in length.

As indicated above, antibodies can be used to detect TRPC6 proteins in general, or particular variants. Antibodies can be selected to preferentially bind to particular variants relative to wild-type. The amount of the binding preference may be at least two-fold, at least five-fold, at least ten-fold, or at least twenty-fold. One antibody which is particularly useful is one which preferentially binds to the P112Q variant relative to the wild-type. An antibody with the converse specificity may also be diagnostically useful. Antibodies according to the invention can be polyclonal or monoclonal. Methods of making both types of antibodies are well known in the art. Typically generating antibodies of either type begins with immunization of a sheep, rabbit, mouse, goat, etc., with a specific immunogen which is enriched for the antigen or epitope to which antibodies are desired. Adjuvants may also be used to enhance the immune response to the immunogen. Antibodies can be labeled with a moiety which facilitates detection. Such moieties include enzymatic, radioactive, fluorescent, and luminescent moieties.

Determining the presence of a mutant form of TRPC6 may be useful, as described above, to identify affected individuals prior to the manifestation of symptoms. In addition, identification of mutation carriers may be useful in assigning patients to treatment regimes. For example, a patient with an P112Q variant is an excellent candidate for receiving TRPC6 inhibitor therapy. In addition, identification of a TRPC6 mutation can be used during clinical trials to stratify patients for drug testing.

Mutations in several other proteins have been identified in familial nephrotic syndrome and hereditary FSGS. Nephrin (NPHS1), the cause of Finnish nephropathy, is a protein of unknown function that localizes to the glomerular slit diaphragm and appears to form a "zipper-like structure" (20). Podocin (NPHS2) appears to anchor elements of the slit diaphragm to the cytoskeleton (21). Lastly, mutations in alpha-actinin 4 (ACTN4) may alter functions of the actin cytoskeleton in the podocyte (6, 22). CD2-associated protein (CD2AP) has been implicated in glomerular function on the basis of mouse studies (23). CD2AP also appears to have important interactions with nephrin and podocin at the slit diaphragm.

TRP channels have become the object of intense interest as their role in diverse biological functions emerge. They have been associated with cell growth, ion homeostasis, mechanosensation and PLC-dependent calcium entry into cells. Interestingly, calcium as a second messenger affects many of these same cellular functions. Although the applicants do not wish to be bound by any particular theory or mechanism of operation, the exaggerated calcium signaling conferred by the TRPC6$^{P112Q}$ mutation may disrupt glomerular cell function or may cause apoptosis (24). Moreover, the mutant TRPC6$^{P112Q}$ protein may amplify injurious signals triggered by ligands such as angiotensin II that promote kidney injury and proteinuria.

Clinical manifestations of renal disease do not appear until the 3$^{rd}$ decade in individuals with the TRPC6$^{P112Q}$ mutation. This contrasts with Finnish nephropathy and steroid-resistant nephrotic syndrome, whose sufferers typically develop proteinuria in utero or at birth (5). The delay of onset in those carrying the TRPC6$^{P112Q}$ mutation may reflect the difference between these recessive disorders and the autosomal dominant mechanism of inheritance in our New Zealand family; the presence of one normal TRPC6 allele may postpone the onset of kidney injury. Patients with autosomal dominant FSGS due to mutations in the ACTN4 gene also have a delayed onset of kidney disease.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Identification of Altered Gene in Affected Kindred

Haplotype analyses reduced the minimal candidate region to an approximate 2.1 centiMorgan (cM) area defined by critical recombination events at D11S1390 and D11S1762 (FIG. 1A). This region contains several known genes as well as multiple novel and predicted genes which were systematically screened for mutations by direct sequencing. After examination of 42 other candidate genes, TRPC6 (GenBank Accession No. NP_004612) emerged as a candidate based on reports of detection of TRPC6 mRNA in the kidney (9, 10). We therefore sequenced each of the 13 exons of the TRPC6 gene along with their intron/exon boundaries. Primer sequences are provided (FIG. 9). As shown in FIG. 1B, we discovered a missense mutation (C335A) in exon 2, from affected individuals, causing a proline to glutamine substitution at position 112 within the first ankyrin repeat of the TRPC6 protein. This variant was present in all of the affected individuals (20 affected; 1 probably affected) in our kindred and there were no non-penetrant carriers. The change was not found in any of the public single nucleotide polymorphism (SNP) databases. Furthermore, we found no evidence of the substitution in 614 chromosomes screened from a group of Caucasian controls without known renal disease, 33 of whom were from New Zealand. The allele frequencies from all markers used for linkage in this kindred and the New Zealand controls are similar to those in the other Caucasian controls. Proline 112 is highly conserved in evolution and is present in TRPC protein homologues from multiple species (FIG. 5).

EXAMPLE 2

Figures 2A, 2B, 2C, 2D, 2E, 2F:
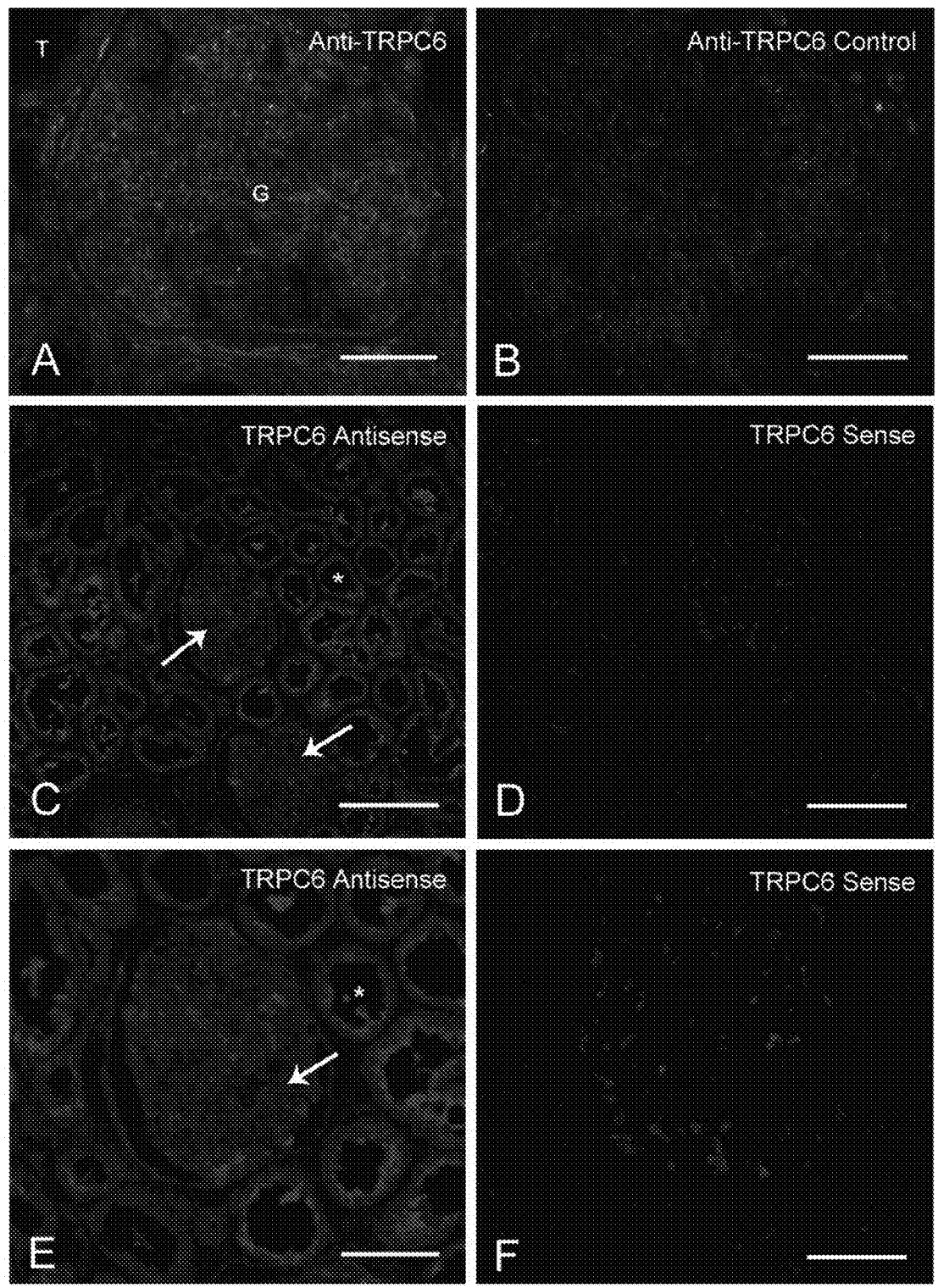
FIGS. 2A-2F. Immunofluorescence staining and fluorescent in-situ hybridization of normal human renal cortical tissue for TRPC6.

Immunohistological Determination of Protein Expression and FISH Determination of mRNA Expression Our previous finding that familial FSGS does not recur in affected patients after renal transplantation indicates a critical role for the kidney in disease pathogenesis (11). While expression of TRPC6 mRNA has been reported in multiple tissues including the kidney, its distribution in kidney is not clear (9, 10). Therefore, to define the spatial distribution of TRPC6 protein expression in human kidney, we performed immunohistochemistry of normal human renal cortex with rabbit antibody raised against a specific human TRPC6 peptide (FIGS. 2A and 2B). Immunofluorescence staining revealed TRPC6 expression throughout the kidney in glomeruli and tubules. This is consistent with a recent study detecting TRPC6 mRNA in isolated glomeruli (12). Expression of TRPC6 in glomeruli is particularly noteworthy as abnormal podocyte function appears to be a final common pathway in a variety of proteinuric kidney diseases (13). To verify these immunofluorescence findings, we carried out fluorescent in situ hybridization (FISH) in human kidney sections (FIGS. 2C-2F). These studies confirmed diffuse expression of TRPC6 mRNA in glomeruli and tubules in a pattern that is virtually identical to that seen with anti-TRPC6 antibody staining.

EXAMPLE 3

Mutation Activates Channel Activity

Figures 3A, 3B, 3C, 3D:
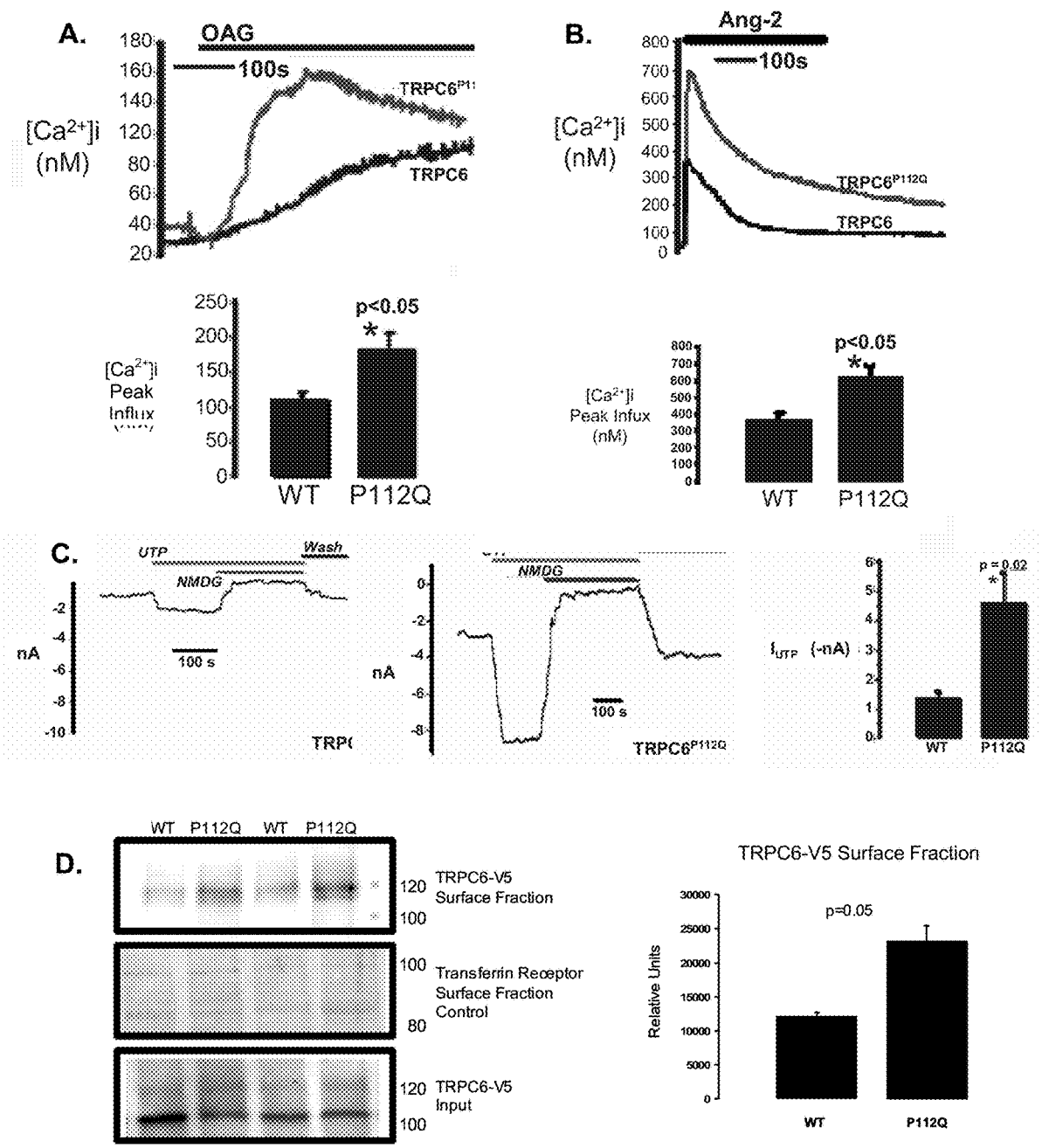
FIGS. 3A-3D. The TRPC6$^{P112Q}$ mutant enhances the influx of calcium into cells via DAG-mediated and receptor-operated pathways.
Figure 4:
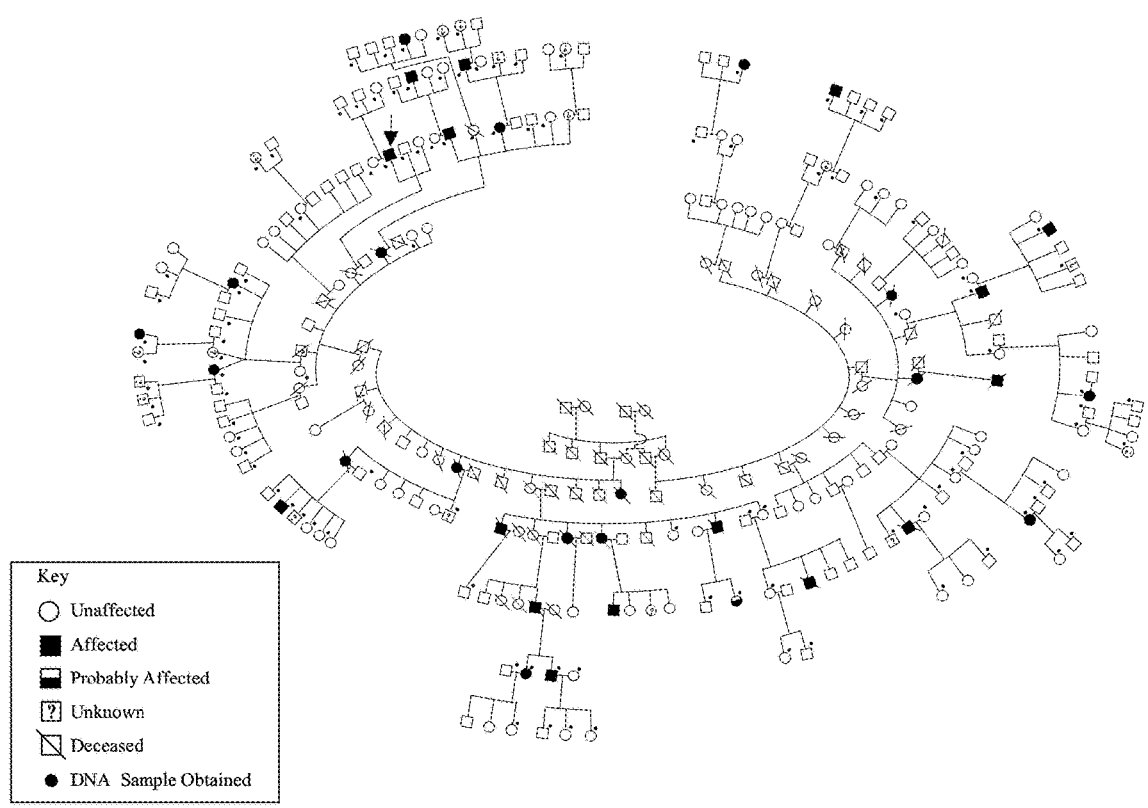
FIG. 4. Simplified version of pedigree for family 6530. Apparent autosomal dominant inheritance. Family structures have been changed for anonymity (1).

To determine the effect of the P112Q mutation on TRPC6 function, we studied HEK 293 cells (human kidney cells) transfected with mutant (TRPC6$^{P112Q}$) or wild-type (WT) TRPC6 (14). The WT TRPC6 was cloned from a human kidney cDNA library. On Western blots, the abundance and mobility of the P112Q mutant was comparable to that of WT TRPC6 (FIG. 6). Diacylglycerol (DAG) is a potent activator of TRPC6 (15). We therefore measured the intracellular calcium concentration ([Ca$^{+2}$]i) using Fura fluorescence in HEK 293 cells expressing either the WT or TRPC6$^{P112Q}$ after exposure to the DAG analogue OAG (1-oleoyl-2-acetyl-sn-glycerol). OAG perfusion increased late Ca$^{+2}$ transients in cells transfected with WT TRPC6 as expected (FIGS. 3A and FIG. 7). Peak intracellular concentrations were significantly higher in cells expressing the TRPC6$^{P112Q}$ compared with WT controls ([Ca$^{2+}$]i TRPC6$^{P112Q}$=181±25 nM vs. [Ca$^2$]i WT TRPC6=106±15 nM; p<0.05).

EXAMPLE 4

Mutation Enhances Receptor-Operated Calcium Signaling

Angiotensin II acting through its AT1 receptor plays a critical role in the generation of proteinuria and progression of kidney injury in a number of kidney diseases including FSGS (16). AT1 receptors, coupled to heterotrimeric G nucleotide-binding proteins, activate phospholipase C-beta isoforms that hydrolyze phosphatidylinositol 4,5-bisphosphate (PIP$_2$). This triggers production of inositol 1,4,5-trisphosphate (InsP$_3$) and diacylglycerol (DAG) releases internal calcium stores and activates Ca$^{+2}$ entry, respectively (17). We examined whether the P112Q mutation would affect angiotensin II-dependent (i.e., receptor-operated) calcium signaling. HEK 293 cells were co-transfected with the AT1 angiotensin receptor (AT-YFP) and either WT TRPC6 or TRPC6$^{P112Q}$. [Ca$^{+2}$], changes were measured after exposure to angiotensin II (FIGS. 3B and FIG. 8); similar to the OAG experiments, the peak angiotensin II-stimulated [Ca$^{+2}$]$_i$ was higher in cells expressing the mutant protein compared with WT controls ([Ca$^{2+}$]i TRPC6$^{P112Q}$=640±66 nM vs. [Ca$^{2+}$]i WT TRPC6=357±46 nM; p<0.05). To establish that the P112Q mutation is not isolated to TRPC6 channels, we introduced the analogous mutation into the TRPC3 channel. Our results demonstrate the same augmented Ca$^{+2}$ entry observed with the TRPC6$^{P112Q}$ mutation.

EXAMPLE 5

Mutation Increases Surface Expression of TRPC6

We also evaluated the subcellular localization of the mutant TRPC6 protein by performing surface biotinylation experiments (FIG. 3D). These confirmed that the relative distribution of TRPC6$^{P112}$Q protein in the plasma membrane was significantly greater than the wild-type protein (densitometry—WT TRPC6=1210.33 vs. TRPC6$^{P112Q}$=23126.67 units; p=0.05). Because the transferrin receptor (TfR) is constitutively expressed on the cell surface, we probed the cell surface fraction with an antibody to TfR as a control. No difference was found in the surface expression of TfR in cells transfected with either WT TRPC6 or TRPC6$^{P112Q}$. Likewise, we probed the cell surface fraction with antibody to the cytosolic protein actin and found no non-specific labeling of intracellular proteins. Our findings are in accordance with reports by others (18, 19). This enhanced cell surface expression of TRPC6$^{P112Q}$ protein suggests a mechanism of exaggerated calcium signaling and flux.

EXAMPLE 6

Materials and Methods

Ascertainment and Diagnostic Criteria

The ascertainment and clinical diagnosis are as previously described (1). Family 6530 was initially identified by the Department of Nephrology, Christchurch Hospital, Christchurch, New Zealand. All available renal biopsies and biopsy reports were independently reviewed by D.N.H. Evaluation of the family included a complete family history and an assay of serum creatinine and urinalysis where appropriate. Asymptomatic individuals were examined for proteinuria with qualitative urinalysis. The Duke University Medical Center (Durham, N.C.) Institutional Review Board and the Canterbury Ethics Committee approved this project and all participants gave signed informed consent prior to data and DNA collection.

Haplotype Analysis

Haplotype analysis was performed as previously described to identify critical recombination events (2). The haplotypes were constructed via visual inspection and by SIMWALK2 computerized haplotyping algorithm. Genetic and physical map distances as well as marker order were obtained from public databases (websites at genome.cse.ucsc.edu and research.marshfieldclinic.org/genetics/).

DNA Isolation and Genotyping

Genomic DNA was isolated from peripheral blood through the Center for Human Genetics, Duke University Medical Center using PureGene™ (Gentra). Genotyping was carried out as described by Vance et al., (3). Microsatellite markers within the area of interest were identified from a variety of sources, including, ensembl.org, and genome.cse.ucsc.edu. A Hitachi FMBIOII was used for detection, data was processed using BioImage® and databased using Pedigene® (4).

TRPC6 Sequencing and Mutation Detection

TRPC6 exons were amplified using the polymerase chain reaction (PCR) with primers that were designed using the Primer 3 design software (website at genome.wi.mit.edu/cgi-bin/primer/primer3_www.cgi) from known genomic sequence (website at genome.cse.ucsc.edu) using standard PCR protocols. Both strands of DNA were sequenced. Targeted sequence included all exons and 25-50 base pairs of the intronic sequence surrounding each exon. PCR products were purified using the QIAquick PCR purification kit (Qiagen). Sequencing reactions were performed using BigDye® Terminator V3.1 Cycle Sequencing Kit (Applied Biosystems) and purified using Edge Biosystems Gel Filtration Columns (Edge Biosystems). Sequencing was carried out using the ABI 3730 DNA Analyzer (Applied Biosystems) and analyzed using Sequencher DNA sequencing analysis software (Gene Codes Corporation).

Immunofluorescent Staining

Normal human renal tissue was embedded in gelatin, snap frozen in liquid-nitrogen-cooled 2-methylbutane, and stored at −85° C. Frozen sections were cut at 4 µm, air dried, and fixed in acetone. For immunofluorescent staining, sections were incubated for 30-min at 25° C. with rabbit anti-TRPC6 (Chemicon) at a dilution of 1:50 and a mouse anti-synaptopodin monoclonal antibody (Progen Biotechnik GmBH) at 1:64 in phosphate-buffered saline, pH 7.4 (PBS) supplemented with 1% bovine serum albumin (PBS/BSA). The TRPC6 antibody was raised against a 16-amino-acid peptide that is identical to the human TRPC6 sequence in 15 of 16 residues (Mouse Peptide—RRNESQDYLLMDELG; SEQ ID NO: 68). The immunizing peptide does not align with any amino acid sequence other than TRPC6 according to a protein BLAST search (website at ncbi.nlm.nih.gov) of the human genome and according to printed material from the companies supplying the antibody. Additionally, we have found that this antibody does not recognize recombinant TRPC3, one of the members of the TRPC3/6/7 subfamily, on Western blot. The synaptopodin antibody has been well-characterized (5). Following two washes with PBS, biotinylated goat-anti-rabbit IgG (Jackson ImmunoResearch Laboratories, Inc.) at a dilution of 1:400 and Cy3-conjugated donkey-anti-mouse IgG at 1:400 in PBS/BSA were added. After an additional 30-min incubation and two washes with PBS, Cy2-conjugated streptavidin (Jackson ImmunoResearch Laboratories) at a dilution of 1:400 was added. Following a final 30-min incubation and two additional washes with PBS, the sections were mounted with 80% glycerol in 0.25 M Tris buffer, pH 7.7, and examined using an epifluorescence microscope equipped with green excitation/red emission and blue excitation/green emission filter sets. As negative controls, additional sections were stained in parallel with either pre-immune immunoglobulin of the relevant species or anti-TRPC6 preincubated with a molar excess of the immunizing peptide substituted for the primary antibody. Sections were also incubated with rabbit anti-TRPC6 at a dilution of 1:50 and mouse anti-CD34 (BD Biosciences) at a dilution of 1:400 with staining carried out in the same manner as above.

Fluorescent In Situ Hybridization for TRPC6

Normal human renal tissue was fixed for 16 hours in paraformaldehyde, paraffin embedded, and sections cut at 4-5 microns in thickness. For in situ hybridization, sections were incubated with DIG-labeled probes corresponding to the sense and anti-sense strands of the of TRPC6 cloned from human kidney (Clontech). The probe was generated by digestion of the human kidney cDNA library with EcoRV and BamH1 (corresponding nucleotide 2301-5' TATCACT-TGG . . . (SEQ ID NO: 66); corresponding nucleotide 3621- . . . TTATTTCAGG 3'(SEQ ID NO: 67); accession number AJ006276). The resulting fragment was cloned into pBS. For DIG labeling, probes were generated by in vitro transcription according to the manufacturer's protocol (Roche). Serial washes in SSC were followed by a blocking step with 5% normal rabbit IgG (Dako) RT 30-40 min and then with (1:200) HRP-rabbit anti-DIG Ab RT 45-60 min (Roche). Sections were washed with TBST and then incubated with Cy3 conjugated tyramide for 5 minutes and then coverslipped. Sections were examined using confocal microscopy with a filter set optimized for Cy3. Background staining in the sense hybridization sections reflect autofluorescence from red blood cells trapped at the time of kdney harvest.

Cloning of TRPC6 and Mutagenesis of TRPC6 C335A

The open reading frame of human TRPC6 was cloned by PCR from a human kidney cDNA library (Clontech). PCR primers were designed to amplify several fragments and the overlapping clones were sub-cloned into the mammalian expression vector pcDNA3.1 (Invitrogen) with a CMV promoter. Site-directed mutagenesis was carried out using Quickchange kit (Stratagene) to construct the C335A mutation. The resulting mutant clone was sequenced to confirm the base change as well the entire full-length sequence. Where indicated the ORF for TRPC6 and TRPC6$^{P112Q}$ were cloned into the pEF-V5 expression plasmid (Invitrogen) and pCMV-N1GFP expression plasmid (Clontech) as previously with TRPC3 (6).

Cell Transfection, Surface Expression and Imaging of TRPC6

HEK 293 cells were plated on glass bottom plates at near confluence. After 24 hours, the cells were transfected with plasmids in the presence of lipofectamine 2000 (Invitrogen). Here 3 µg of TRPC6 plasmid (WT or mutant) and 1 µg of ATR-YFP plasmid were incubated for 4 hours in Optimem 2000 media (Gibco) and then changed to 10% FBS/DMEM media. For biotinylation experiments, 24 hours after transfection with TRPC6-V5 and TRPC6$^{P112Q}$-V5 constructs, cells were washed with ice cold PBS and incubated with sulfo-NHS-SS-Biotin (2 mg/ml) (Pierce) for 30-min at 4° C. After 3 washes with PBS with 10 mM glycine, cells were incubated with RIPA lysis buffer for 30-min at 4° C. Lysates were passed through a 20G and then 25G needle for 25 passes. Samples were then collected by centrifuging at 20K G for 15-min at 4° C. Supernatants were then incubated overnight with streptavidin agaraose beads (Pierce), washed 3 times and then heated to 37° C. Samples were then subjected to SDS-PAGE and immunoblotting with an antibody raised against the V5 epitope tag (Invitrogen). Samples were then immunoblotted with a monoclonal anti-transferrin receptor antibody as a control (Sigma-Aldrich). For determining total cellular TRPC6 expression, protein extracts were collected prior to streptavidin bead incubation. For immunostaining experiments, cells were fixed with ice-cold methanol, permeabilized, and incubated with the TRPC6 antibody and followed by a FITC-conjugated secondary antibody. Standard epifluorescence microscopy was used to collect a series of Z images which were then stacked and processed using Metafluor image processing (Universal Imaging).

Single Cell Imaging of Divalent Cations

HEK 293 cells transfected with plasmids (TRPC6, TRPC6$^{P112Q}$ and ATR-YFP) were attached to glass coverslips and loaded with 1-10 µM Fura-2 AM (Molecular Probes) for 45-min. Following a de-esterification period of 30-min, cells were imaged by an epifluorescent microscopy system designed to capture rapid calcium transients as previously described (6). Cells were then stimulated with angiotensin II (1 µM) or 100 µM 1-oleoyl-2-acetyl sn-glycerol (OAG) (Calbiochem) in a barium containing solution. The lambda DG4 (Sutter Instruments) provides for rapid excitation filter changes and 340/380 ratios are captured every 10-100 msec from a Cool SNAP HQ CCD camera (Roper Scientific). All components including the filter selection, stage temperature, shutters and motorized stage are controlled by Metafluor software (Universal Imaging).

Whole Cell Current Recordings and Patch Clamp

HEK 293 were plated on glass coverslips and transfected with TRPC6-GFP and TRPC6$^{P112}$Q-GFP. Bath solution comprised of (in mM): 140 NaCl, 2 BaCl$_2$, 2.8 KCl, 1.0 MgCl$_2$, 10 HEPES, 10 dextrose, adjusted to pH 7.4 with NaOH. For Na$^+$free solution, NaCl was replaced with 140 mM NMDG. The patch pipette solution was comprised of (in mM): 140 Cs aspartate, 5 NaCl, 10 HEPES, 10 BAPTA and 1 Mg$_2$ATP (pH 7.3, KOH). Electrodes were pulled from type 7052 glass (Garner Glass Co.) and had resistances of 2-5 Mohms. The cells were voltage clamped using the whole-cell patch clamp technique (7). The electrodes were fire-polished and coated with Sylgard 184. Offset potentials between the solution and the bath were zeroed prior to seal formation. Currents were measured with a Dagon 3900 amplifier. Data acquisition and voltage pulses were controlled with pClamp 8.0 software and the Digidata 1300 system from Axon Instruments. All patch clamp recordings were at room temperature.

REFERENCES AND NOTES

The disclosure of each reference cited is expressly incorporated herein.

1. T. Srivastava, S. D. Simon, U. S. Alon, *Pediatric Nephrology* 13, 13 (1999).
2. A. Hurtado et al., *Clin. Nephrol.* 53, 325 (2000).
3. S. M. Korbet, R. M. Genchi, R. Z. Borok, M. M. Schwartz, *American Journal of Kidney Diseases* 27, 647 (1996).
4. M. Kestila et al., *Molecular Cell* 1, 575 (1998).
5. N. Boute et al., *Nat. Genet.* 24, 349 (2000).
6. J. M. Kaplan et al., *Nat. Genet.* 24, 251 (2000).
7. M. P. Winn et al., *Kidney Int.* 55, 1241 (1999).
8. M. P. Winn et al., *Genomics* 58, 113 (1999).
9. A. Riccio et al., *Brain Res. Mol. Brain Res.* 109, 95 (2002).
10. R. L. Garcia, W. P. Schilling, *Biochem. Biophys. Res. Commun.* 239, 279 (1997).
11. P. J. Conlon et al., *Kidney Int.* 56, 1863 (1999).
12. C. S. Facemire, P. J. Mohler, W. J. Arendshorst, *Am. J. Physiol Renal Physiol* 286, F546 (2004).
13. P. Mundel, S. J. Shankland, *J. Am. Soc. Nephrol.* 13, 3005 (2002).
14. The HEK293 cell line was originally derived from human embryonic kidney and its morphological features bear little or no resemblance to mature renal cell lineages. Thus, the absence of TRPC6 expression in HEK cells probably has little bearing on whether or not the protein is actually expressed in mature kidney tissue. An example of this phenomenon are the angiotensin receptors which are not expressed in HEK cells but are expressed throughout the kidney.
15. T. Hofmann et al., *Nature* 397, 259 (1999).
16. M. W. Taal, B. M. Brenner, *Kidney Int.* 57, 1803 (2000).
17. T. Balla, P. Varnai, Y. Tian, R. D. Smith, *Endocr. Res.* 24, 335 (1998).
18. B. B. Singh et al., *Mol. Cell* 15, 635 (2004).
19. V. J. Bezzerides, I. S. Ramsey, S. Kotecha, A. Greka, D. E. Clapham, *Nat. Cell Biol.* 6, 709 (2004).
20. V. Ruotsalainen et al., *Proc. Natl. Acad. Sci. U. S. A* 96, 7962 (1999).
21. S. Roselli et al., *Am. I Pathol.* 160, 131 (2002).
22. C. H. Kos et al., *J. Clin. Invest* 111, 1683 (2003).
23. K. Schwarz et al., *J. Clin. Invest* 108, 1621 (2001).
24. Y. Hara et al., *Mol. Cell* 9, 163 (2002).

Supporting Reference List for Example 6

1. M. P. Winn et al., *Genomics* 58, 113 (1999).
2. M. A. Pericak-Vance, in *Current Protocols in Human Genetics*, N. C. Dracopoli et al., Eds. (John Wiley And Sons, Inc., New York, 1997), p. 1.
3. J. M. Vance, K. Ben Othmane, in *Approaches to Gene Mapping in Complex Human Diseases*, J. L. Haines, M. A. Pericak-Vance, Eds. (Wiley-Liss, New York, 1998), pp. 213-228.
4. C. Haynes et al., paper presented at Am J Human Genet 1995.
5. L. Barisoni et al., *Kidney Int.* 58, 137 (2000).
6. P. Rosenberg et al., *Proc. Natl. Acad. Sci. U. S. A* 101, 9387 (2004).
7. T. L. Creazzo, J. Burch, R. E. Godt, *Biophys. J.* 86, 966 (2004).
8. A. Dietrich et al., *J. Biol. Chem.* 278, 47842 (2003).
9. G. Vazquez, B. J. Wedel, M. Trebak, B. G. St John, J. W. Putney, Jr., *J. Biol. Chem.* 278, 21649 (2003).

We claim:

1. A method of detecting a mutation in a human Transient Receptor Potential Cation Channel, Subfamily C, Member 6 (TRPC6) gene in a sample from a human individual, comprising:
    (a) contacting a sample comprising a TRPC6 polynucleotide from a human with an oligonucleotide probe, wherein the probe specifically binds to a portion of the nucleotide sequence of SEQ ID NO: 64 including position 762 of the nucleotide sequence of SEQ ID NO: 64, and wherein the probe is detectably labeled with a moiety selected from the group consisting of: enzymatic, radioactive, fluorescent, and luminescent moieties;
    (b) hybridizing the probe to the TRPC6 polynucleotide; and
    (c) detecting hybridization of the probe to the TRPC6 polynucleotide, wherein hybridization is indicative of the presence of a mutation in the TRPC6 gene in the sample.

2. The method of claim 1, wherein the mutation in the TRPC6 gene is a C>A substitution corresponding to position 762 of the nucleotide sequence of SEQ ID NO: 64.

3. The method of claim 1, wherein the mutation in the TRPC6 gene encodes a mutation corresponding to position 112 of the amino acid sequence of SEQ ID NO: 63 or the amino acid sequence of SEQ ID NO: 65.

4. The method of claim 3, wherein the mutation in the TRPC6 gene encodes a P>Q substitution corresponding to position 112 of the amino acid sequence of SEQ ID NO: 63 or the amino acid sequence of SEQ ID NO: 65.

5. The method of claim 1, wherein the probe comprises a polynucleotide comprising a contiguous portion of the polynucleotide sequence of SEQ ID NO: 64 including position 762 of the polynucleotide sequence of SEQ ID NO: 64 or the complementary sequence thereof.

6. The method of claim 1, wherein the probe is at least 15 nucleotides.

7. The method of claim 1, wherein the probe comprises a polynucleotide sequence encoding a polypeptide comprising at least six contiguous amino acid residues of human TRPC6 amino acid sequence.

8. The method of claim 1, wherein the probe comprises at least 18 contiguous nucleotides that are complementary to a human TRPC6 sequence comprising the nucleotide sequence of SEQ ID NO: 64.

* * * * *

SEQUENCE LISTING

```
<160> NUMBER OF SEQ ID NOS: 68

<210> SEQ ID NO 1
<211> LENGTH: 72
<212> TYPE: PRT
<213> ORGANISM: Homo sapiens

<400> SEQUENCE: 1

Arg Leu Ala Asn Arg Gly Pro Ala Tyr Met Phe Ser Asp Arg Ser Thr
1               5                   10                  15
```

Ser Leu Ser Ile Glu Glu Glu Arg Phe Leu Asp Ala Ala Glu Tyr Gly
            20                  25                  30

Asn Ile Pro Val Val Arg Lys Met Leu Glu Glu Cys His Ser Leu Asn
        35                  40                  45

Val Asn Cys Val Asp Tyr Met Gly Gln Asn Ala Leu Gln Leu Ala Val
    50                  55                  60

Ala Asn Glu His Leu Glu Ile Thr
65                  70

<210> SEQ ID NO 2
<211> LENGTH: 72
<212> TYPE: PRT
<213> ORGANISM: Mus musculus

<400> SEQUENCE: 2

Arg Leu Ala Asn Arg Gly Pro Ala Tyr Met Phe Asn Asp His Ser Thr
1               5                   10                  15

Ser Leu Ser Ile Glu Glu Glu Arg Phe Leu Asp Ala Val Glu Tyr Gly
            20                  25                  30

Asn Ile Pro Val Val Trp Lys Met Leu Glu Glu Cys His Ser Leu Asn
        35                  40                  45

Val Asn Cys Val Asp Tyr Met Gly Gln Asn Ala Leu Gln Leu Ala Val
    50                  55                  60

Ala Asn Glu His Leu Glu Ile Thr
65                  70

<210> SEQ ID NO 3
<211> LENGTH: 72
<212> TYPE: PRT
<213> ORGANISM: Rattus norvegicus

<400> SEQUENCE: 3

Arg Leu Ala Asn Arg Gly Pro Ala Tyr Met Phe Asn Asp His Ser Thr
1               5                   10                  15

Ser Leu Ser Ile Glu Glu Glu Arg Phe Leu Asp Ala Ala Glu Tyr Gly
            20                  25                  30

Asn Ile Pro Val Val Arg Lys Met Leu Glu Glu Cys Leu Ser Leu Asn
        35                  40                  45

Val Asn Cys Val Asp Tyr Met Gly Gln Asn Ala Leu Gln Leu Ala Val
    50                  55                  60

Ala Asn Glu His Leu Glu Ile Thr
65                  70

<210> SEQ ID NO 4
<211> LENGTH: 72
<212> TYPE: PRT
<213> ORGANISM: Cavia porcellus

<400> SEQUENCE: 4

Arg Leu Ala Asn Arg Gly Pro Ala Tyr Met Phe Asn Asp His Ser Thr
1               5                   10                  15

Thr Leu Ser Ile Glu Glu Glu Arg Phe Leu Asp Ala Ala Glu Tyr Gly
            20                  25                  30

Asn Ile Pro Val Val Arg Lys Met Leu Glu Glu Cys Leu Ser Leu Asn
        35                  40                  45

Val Asn Cys Val Asp Tyr Met Gly Gln Asn Ala Leu Gln Leu Ala Val
    50                  55                  60

Ala Asn Glu His Leu Glu Ile Thr

```
65                  70

<210> SEQ ID NO 5
<211> LENGTH: 75
<212> TYPE: PRT
<213> ORGANISM: Drosophila melanogaster

<400> SEQUENCE: 5

Ala Pro Lys Ser Val Gly Gly Cys Cys Val Pro Leu Gly Leu Pro Gln
1               5                   10                  15

Pro Leu Leu Leu Glu Glu Lys Lys Phe Leu Leu Ala Val Glu Arg Gly
            20                  25                  30

Asp Met Pro Asn Val Arg Arg Ile Leu Gln Lys Ala Leu Arg His Gln
        35                  40                  45

His Ile Asn Ile Asn Cys Met Asp Pro Leu Gly Arg Arg Ala Leu Thr
    50                  55                  60

Leu Ala Ile Asp Asn Glu Asn Leu Glu Met Val
65                  70                  75

<210> SEQ ID NO 6
<211> LENGTH: 76
<212> TYPE: PRT
<213> ORGANISM: Caenorhabditis elegans

<400> SEQUENCE: 6

Arg Lys Ser Arg Val Lys Ser Leu Lys His Ala Gln Leu Leu His Gly
1               5                   10                  15

Tyr Tyr Ile Leu Ser Asn Asn Leu Phe Arg Phe Leu Glu Ala Ala Glu
            20                  25                  30

Leu Gly Asn Lys Pro Thr Leu Gln Glu Cys Leu Asp Tyr Asp Gly Asp
        35                  40                  45

Arg Arg Leu Asn Val Asn Cys Leu Asp Ser Met Gly Arg Thr Ala Leu
    50                  55                  60

Glu Ile Ala Val Asp Asn Glu Asn Met Glu Val Val
65                  70                  75

<210> SEQ ID NO 7
<211> LENGTH: 30
<212> TYPE: DNA
<213> ORGANISM: Homo sapiens

<400> SEQUENCE: 7
cctcctagtt caggctcata ccgcctcctg                                    30

<210> SEQ ID NO 8
<211> LENGTH: 25
<212> TYPE: DNA
<213> ORGANISM: Homo sapiens

<400> SEQUENCE: 8
acgacggtga agcagggggt gcaga                                         25

<210> SEQ ID NO 9
<211> LENGTH: 27
<212> TYPE: DNA
<213> ORGANISM: Homo sapiens

<400> SEQUENCE: 9
taagtggtga cttttccccg ggccagt                                       27
```

```
<210> SEQ ID NO 10
<211> LENGTH: 27
<212> TYPE: DNA
<213> ORGANISM: Homo sapiens

<400> SEQUENCE: 10
cctaggaggt acacacgcgg gttcagg                                        27

<210> SEQ ID NO 11
<211> LENGTH: 20
<212> TYPE: DNA
<213> ORGANISM: Homo sapiens

<400> SEQUENCE: 11
gcaaagtgct tggctttctt                                                20

<210> SEQ ID NO 12
<211> LENGTH: 20
<212> TYPE: DNA
<213> ORGANISM: Homo sapiens

<400> SEQUENCE: 12
cattctggcc catgtaatcc                                                20

<210> SEQ ID NO 13
<211> LENGTH: 20
<212> TYPE: DNA
<213> ORGANISM: Homo sapiens

<400> SEQUENCE: 13
cgtgagaagg ggagaaggtt                                                20

<210> SEQ ID NO 14
<211> LENGTH: 20
<212> TYPE: DNA
<213> ORGANISM: Homo sapiens

<400> SEQUENCE: 14
attgcttcca caatccgaac                                                20

<210> SEQ ID NO 15
<211> LENGTH: 20
<212> TYPE: DNA
<213> ORGANISM: Homo sapiens

<400> SEQUENCE: 15
agaatgccac tcactcaacg                                                20

<210> SEQ ID NO 16
<211> LENGTH: 20
<212> TYPE: DNA
<213> ORGANISM: Homo sapiens

<400> SEQUENCE: 16
tggagtcaca tcatgggaga                                                20

<210> SEQ ID NO 17
<211> LENGTH: 20
<212> TYPE: DNA
<213> ORGANISM: Homo sapiens

<400> SEQUENCE: 17
gttcggattg tggaagcaat                                                20
```

```
<210> SEQ ID NO 18
<211> LENGTH: 20
<212> TYPE: DNA
<213> ORGANISM: Homo sapiens

<400> SEQUENCE: 18
tggagtggct aaacgagtca                                              20

<210> SEQ ID NO 19
<211> LENGTH: 20
<212> TYPE: DNA
<213> ORGANISM: Homo sapiens

<400> SEQUENCE: 19
ctcccatgat gtgactccaa                                              20

<210> SEQ ID NO 20
<211> LENGTH: 20
<212> TYPE: DNA
<213> ORGANISM: Homo sapiens

<400> SEQUENCE: 20
gcttgtggag ggtgaagtct                                              20

<210> SEQ ID NO 21
<211> LENGTH: 20
<212> TYPE: DNA
<213> ORGANISM: Homo sapiens

<400> SEQUENCE: 21
tgactcgttt agccactcca                                              20

<210> SEQ ID NO 22
<211> LENGTH: 18
<212> TYPE: DNA
<213> ORGANISM: Homo sapiens

<400> SEQUENCE: 22
ctgagcacat gggggaag                                                18

<210> SEQ ID NO 23
<211> LENGTH: 23
<212> TYPE: DNA
<213> ORGANISM: Homo sapiens

<400> SEQUENCE: 23
tctgaagcat agtaaaacgt ggt                                          23

<210> SEQ ID NO 24
<211> LENGTH: 24
<212> TYPE: DNA
<213> ORGANISM: Homo sapiens

<400> SEQUENCE: 24
ccctttatcc ttatttagca ccaa                                         24

<210> SEQ ID NO 25
<211> LENGTH: 20
<212> TYPE: DNA
<213> ORGANISM: Homo sapiens

<400> SEQUENCE: 25
gccatttgtt tgttgcctgt                                              20
```

```
<210> SEQ ID NO 26
<211> LENGTH: 20
<212> TYPE: DNA
<213> ORGANISM: Homo sapiens

<400> SEQUENCE: 26
acccaactgt gattccctga                                               20

<210> SEQ ID NO 27
<211> LENGTH: 21
<212> TYPE: DNA
<213> ORGANISM: Homo sapiens

<400> SEQUENCE: 27
ggagatcatt ggaatgtgca g                                             21

<210> SEQ ID NO 28
<211> LENGTH: 20
<212> TYPE: DNA
<213> ORGANISM: Homo sapiens

<400> SEQUENCE: 28
aatgaaccca aggcaactgt                                               20

<210> SEQ ID NO 29
<211> LENGTH: 21
<212> TYPE: DNA
<213> ORGANISM: Homo sapiens

<400> SEQUENCE: 29
caggctgaga cctttcaaac a                                             21

<210> SEQ ID NO 30
<211> LENGTH: 24
<212> TYPE: DNA
<213> ORGANISM: Homo sapiens

<400> SEQUENCE: 30
tgcagtaacc gaactactac tgac                                          24

<210> SEQ ID NO 31
<211> LENGTH: 21
<212> TYPE: DNA
<213> ORGANISM: Homo sapiens

<400> SEQUENCE: 31
ggagacttcc attcgaaaac c                                             21

<210> SEQ ID NO 32
<211> LENGTH: 24
<212> TYPE: DNA
<213> ORGANISM: Homo sapiens

<400> SEQUENCE: 32
tgcaccaatg tagtaggagt agag                                          24

<210> SEQ ID NO 33
<211> LENGTH: 19
<212> TYPE: DNA
<213> ORGANISM: Homo sapiens

<400> SEQUENCE: 33
```

```
ggacccctct gatcctcaa                                              19

<210> SEQ ID NO 34
<211> LENGTH: 22
<212> TYPE: DNA
<213> ORGANISM: Homo sapiens

<400> SEQUENCE: 34
agagtccctc caactcattt gt                                          22

<210> SEQ ID NO 35
<211> LENGTH: 20
<212> TYPE: DNA
<213> ORGANISM: Homo sapiens

<400> SEQUENCE: 35
ccatccttgc agcaatccta                                             20

<210> SEQ ID NO 36
<211> LENGTH: 20
<212> TYPE: DNA
<213> ORGANISM: Homo sapiens

<400> SEQUENCE: 36
gaatgaacaa agggcgaaga                                             20

<210> SEQ ID NO 37
<211> LENGTH: 20
<212> TYPE: DNA
<213> ORGANISM: Homo sapiens

<400> SEQUENCE: 37
cgatcactgg ggtctgagag                                             20

<210> SEQ ID NO 38
<211> LENGTH: 20
<212> TYPE: DNA
<213> ORGANISM: Homo sapiens

<400> SEQUENCE: 38
aaagggatgt ggcatagtgg                                             20

<210> SEQ ID NO 39
<211> LENGTH: 20
<212> TYPE: DNA
<213> ORGANISM: Homo sapiens

<400> SEQUENCE: 39
agggaagaac cccgtaagaa                                             20

<210> SEQ ID NO 40
<211> LENGTH: 22
<212> TYPE: DNA
<213> ORGANISM: Homo sapiens

<400> SEQUENCE: 40
gcttctgaac atctgtccct tt                                          22

<210> SEQ ID NO 41
<211> LENGTH: 24
<212> TYPE: DNA
<213> ORGANISM: Homo sapiens

<400> SEQUENCE: 41
```

-continued ctcagacaac ctctaacaaa cagc    24

<210> SEQ ID NO 42
<211> LENGTH: 20
<212> TYPE: DNA
<213> ORGANISM: Homo sapiens

<400> SEQUENCE: 42
caaaatgcct ggtacatggt    20

<210> SEQ ID NO 43
<211> LENGTH: 20
<212> TYPE: DNA
<213> ORGANISM: Homo sapiens

<400> SEQUENCE: 43
ggctcactac agggaggaag    20

<210> SEQ ID NO 44
<211> LENGTH: 18
<212> TYPE: DNA
<213> ORGANISM: Homo sapiens

<400> SEQUENCE: 44
gctctccagg cactctgc    18

<210> SEQ ID NO 45
<211> LENGTH: 20
<212> TYPE: DNA
<213> ORGANISM: Homo sapiens

<400> SEQUENCE: 45
tttcctcctg tcccacagtc    20

<210> SEQ ID NO 46
<211> LENGTH: 20
<212> TYPE: DNA
<213> ORGANISM: Homo sapiens

<400> SEQUENCE: 46
gcccattggc acttaagaaa    20

<210> SEQ ID NO 47
<211> LENGTH: 21
<212> TYPE: DNA
<213> ORGANISM: Homo sapiens

<400> SEQUENCE: 47
tctccgctat gaactccttg a    21

<210> SEQ ID NO 48
<211> LENGTH: 20
<212> TYPE: DNA
<213> ORGANISM: Homo sapiens

<400> SEQUENCE: 48
acccattttc aggcagacac    20

<210> SEQ ID NO 49
<211> LENGTH: 20
<212> TYPE: DNA
<213> ORGANISM: Homo sapiens

```
<400> SEQUENCE: 49
ggcccacctt ttaaacaaga                                              20

<210> SEQ ID NO 50
<211> LENGTH: 20
<212> TYPE: DNA
<213> ORGANISM: Homo sapiens

<400> SEQUENCE: 50
aaaaccgcat ggggagtaac                                              20

<210> SEQ ID NO 51
<211> LENGTH: 22
<212> TYPE: DNA
<213> ORGANISM: Homo sapiens

<400> SEQUENCE: 51
tgttcagggt aaaggctgta ga                                           22

<210> SEQ ID NO 52
<211> LENGTH: 21
<212> TYPE: DNA
<213> ORGANISM: Homo sapiens

<400> SEQUENCE: 52
tgcattgagg gataagtagg g                                            21

<210> SEQ ID NO 53
<211> LENGTH: 20
<212> TYPE: DNA
<213> ORGANISM: Homo sapiens

<400> SEQUENCE: 53
tgcggttttt cctctgaagt                                              20

<210> SEQ ID NO 54
<211> LENGTH: 20
<212> TYPE: DNA
<213> ORGANISM: Homo sapiens

<400> SEQUENCE: 54
catgtttcca gggttcagtg                                              20

<210> SEQ ID NO 55
<211> LENGTH: 22
<212> TYPE: DNA
<213> ORGANISM: Homo sapiens

<400> SEQUENCE: 55
ccctacttat ccctcaatgc ac                                           22

<210> SEQ ID NO 56
<211> LENGTH: 20
<212> TYPE: DNA
<213> ORGANISM: Homo sapiens

<400> SEQUENCE: 56
tggaaccaaa caaccacagt                                              20

<210> SEQ ID NO 57
<211> LENGTH: 20
<212> TYPE: DNA
<213> ORGANISM: Homo sapiens
```

<400> SEQUENCE: 57
ttttgtgtgt gtgcgtgtgt                                                    20

<210> SEQ ID NO 58
<211> LENGTH: 20
<212> TYPE: DNA
<213> ORGANISM: Homo sapiens

<400> SEQUENCE: 58
cctctgaatg ccaatggtct                                                    20

<210> SEQ ID NO 59
<211> LENGTH: 20
<212> TYPE: DNA
<213> ORGANISM: Homo sapiens

<400> SEQUENCE: 59
gccatttctg ggagcattta                                                    20

<210> SEQ ID NO 60
<211> LENGTH: 21
<212> TYPE: DNA
<213> ORGANISM: Homo sapiens

<400> SEQUENCE: 60
gccaaagttg gagctaaaca g                                                  21

<210> SEQ ID NO 61
<211> LENGTH: 22
<212> TYPE: DNA
<213> ORGANISM: Homo sapiens

<400> SEQUENCE: 61
ctgatcatgt gaagtggtgt ct                                                 22

<210> SEQ ID NO 62
<211> LENGTH: 20
<212> TYPE: DNA
<213> ORGANISM: Homo sapiens

<400> SEQUENCE: 62
ggatgaaggt ccatctctcg                                                    20

<210> SEQ ID NO 63
<211> LENGTH: 931
<212> TYPE: PRT
<213> ORGANISM: Homo sapiens

<400> SEQUENCE: 63

Met Ser Gln Ser Pro Ala Phe Gly Pro Arg Arg Gly Ser Ser Pro Arg
1               5                   10                  15

Gly Ala Ala Gly Ala Ala Ala Arg Arg Asn Glu Ser Gln Asp Tyr Leu
            20                  25                  30

Leu Met Asp Ser Glu Leu Gly Glu Asp Gly Cys Pro Gln Ala Pro Leu
        35                  40                  45

Pro Cys Tyr Gly Tyr Tyr Pro Cys Phe Arg Gly Ser Asp Asn Arg Leu
    50                  55                  60

Ala His Arg Arg Gln Thr Val Leu Arg Glu Lys Gly Arg Arg Leu Ala
65                  70                  75                  80

Asn Arg Gly Pro Ala Tyr Met Phe Ser Asp Arg Ser Thr Ser Leu Ser

```
            85                  90                  95
Ile Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
            115                 120                 125

Val Asp Tyr Met Gly Gln Asn Ala Leu Gln Leu Ala Val Ala Asn Glu
130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
            165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
            195                 200                 205

Tyr Asp Glu Asp Gly Thr Arg Phe Ser His Asp Val Thr Pro Ile Ile
            210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
            275                 280                 285

Ser Ser Glu Asp Pro Val Met Thr Ala Leu Glu Leu Ser Asn Glu Leu
            290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Cys
            325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
            355                 360                 365

Ala Ile Lys Tyr Glu Val Lys Lys Phe Val Ala His Pro Asn Cys Gln
            370                 375                 380

Gln Gln Leu Leu Ser Ile Trp Tyr Glu Asn Leu Ser Gly Leu Arg Gln
385                 390                 395                 400

Gln Thr Met Ala Val Lys Phe Leu Val Val Leu Ala Val Ala Ile Gly
            405                 410                 415

Leu Pro Phe Leu Ala Leu Ile Tyr Trp Phe Ala Pro Cys Ser Lys Met
            420                 425                 430

Gly Lys Ile Met Arg Gly Pro Phe Met Lys Phe Val Ala His Ala Ala
            435                 440                 445

Ser Phe Thr Ile Phe Leu Gly Leu Leu Val Met Asn Ala Ala Asp Arg
450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
            485                 490                 495

Leu Ile Ile Ser Trp Val Ile Gly Met Ile Trp Ala Glu Cys Lys Glu
            500                 505                 510
```

```
Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
        530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
                565                 570                 575

Lys Tyr Tyr Asn Leu Ala Arg Ile Lys Trp Asp Pro Ser Asp Pro Gln
            580                 585                 590

Ile Ile Ser Glu Gly Leu Tyr Ala Ile Ala Val Val Leu Ser Phe Ser
        595                 600                 605

Arg Ile Ala Tyr Ile Leu Pro Ala Asn Glu Ser Phe Gly Pro Leu Gln
        610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
                645                 650                 655

Ser Tyr Tyr Ile Gly Ala Lys Gln Asn Glu Ala Phe Thr Thr Val Glu
            660                 665                 670

Glu Ser Phe Lys Thr Leu Phe Trp Ala Ile Phe Gly Leu Ser Glu Val
        675                 680                 685

Lys Ser Val Val Ile Asn Tyr Asn His Lys Phe Ile Glu Asn Ile Gly
        690                 695                 700

Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
                725                 730                 735

Asp Ala Asp Val Glu Trp Lys Phe Ala Arg Ala Lys Leu Trp Phe Ser
                740                 745                 750

Tyr Phe Glu Glu Gly Arg Thr Leu Pro Val Pro Phe Asn Leu Val Pro
        755                 760                 765

Ser Pro Lys Ser Leu Phe Tyr Leu Leu Leu Lys Leu Lys Lys Trp Ile
        770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
            820                 825                 830

Lys Gln Pro Ser Ile Arg Ser Ser Glu Asp Phe His Leu Asn Ser Phe
        835                 840                 845

Asn Asn Pro Pro Arg Gln Tyr Gln Lys Ile Met Lys Arg Leu Ile Lys
        850                 855                 860

Arg Tyr Val Leu Gln Ala Gln Ile Asp Lys Glu Ser Asp Glu Val Asn
865                 870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Glu Lys Leu Ser Met Glu Pro Asn Gln Glu Glu
        915                 920                 925
```

Thr Asn Arg
    930

<210> SEQ ID NO 64
<211> LENGTH: 4564
<212> TYPE: DNA
<213> ORGANISM: Homo sapiens
<220> FEATURE:
<221> NAME/KEY: CDS
<222> LOCATION: (428)...(1600)

<400> SEQUENCE: 64

```
ccgggatctt gacggagagt gcggggatg aaggcgggag ctgagggctg gagagtctct      60
gttgacatag taactcttca gctccgtctc ccttgctctc cgctcttacg cttcgctacc     120
accagcggcc ccgcctgtgc cctctctgcc cgggcgcccc agacgcatcc tcgcggggtc     180
tcctcggcct gacctgctca ggtcaagatc ctctttgcac cccctaagt ggtgactttt      240 ccccggggcca gtgggcgagc cacttgcggc gggcgtctgc accccctgct tcaccgtcgt    300 ccctgggca ccggtctgcc caggtccagt tcggccgctg acgcgaaccc tccgcaccgg      360
gtccccgctg gaactgccca ctcggctccc ccgggagcgg ggcccaggcc agtcgggcgt    420 tccccgcc atg agc cag agc ccg gcg ttc ggg ccc cgg agg ggc agt tct     469
         Met Ser Gln Ser Pro Ala Phe Gly Pro Arg Arg Gly Ser Ser
         1               5                  10 ccc cgg ggc gct gcc gga gcc gct gcg cgg cgc aac gag agc cag gac     517
Pro Arg Gly Ala Ala Gly Ala Ala Ala Arg Arg Asn Glu Ser Gln Asp
15                  20                  25                  30 tat ctg ctc atg gac tcg gag ctg gga gaa gac ggc tgc ccg caa gcc     565
Tyr Leu Leu Met Asp Ser Glu Leu Gly Glu Asp Gly Cys Pro Gln Ala
                35                  40                  45 ccg ctg cct tgc tac ggc tac tac ccc tgc ttc cgg gga tct gac aac     613
Pro Leu Pro Cys Tyr Gly Tyr Tyr Pro Cys Phe Arg Gly Ser Asp Asn
            50                  55                  60 aga ctg gct cac cgg cgg cag aca gtt ctc cgt gag aag ggg aga agg     661
Arg Leu Ala His Arg Arg Gln Thr Val Leu Arg Glu Lys Gly Arg Arg
65                  70                  75 tta gct aat cga gga cca gca tac atg ttt agt gat cgc tcc aca agc     709
Leu Ala Asn Arg Gly Pro Ala Tyr Met Phe Ser Asp Arg Ser Thr Ser
            80                  85                  90 cta tct ata gag gag gaa cgc ttt ttg gat gca gct gaa tat ggt aac     757
Leu Ser Ile Glu Glu Glu Arg Phe Leu Asp Ala Ala Glu Tyr Gly Asn
95                  100                 105                 110 atc cca gtg gtg cgg aag atg tta gaa gaa tgc cac tca ctc aac gtt     805
Ile Pro Val Val Arg Lys Met Leu Glu Glu Cys His Ser Leu Asn Val
                115                 120                 125 aac tgt gtg gat tac atg ggc cag aat gcc cta cag ttg gca gtg gcc     853
Asn Cys Val Asp Tyr Met Gly Gln Asn Ala Leu Gln Leu Ala Val Ala
            130                 135                 140 aat gag cat ctg gaa att aca gaa ctt ctt ctc aag aaa gaa aac ctc     901
Asn Glu His Leu Glu Ile Thr Glu Leu Leu Leu Lys Lys Glu Asn Leu
145                 150                 155 tct cga gtt ggg gat gct ttg ctt cta gct att agt aaa ggt tat gtt     949
Ser Arg Val Gly Asp Ala Leu Leu Leu Ala Ile Ser Lys Gly Tyr Val
            160                 165                 170 cgg att gtg gaa gca att ctc agt cat ccg gct ttt gct gaa ggc aag     997
Arg Ile Val Glu Ala Ile Leu Ser His Pro Ala Phe Ala Glu Gly Lys
175                 180                 185                 190 agg tta gca acc agc cct agc cag tct gaa ctc cag caa gat gat ttt    1045
Arg Leu Ala Thr Ser Pro Ser Gln Ser Glu Leu Gln Gln Asp Asp Phe
                195                 200                 205
```

```
tat gcc tat gat gaa gat ggg aca cgg ttc tcc cat gat gtg act cca    1093
Tyr Ala Tyr Asp Glu Asp Gly Thr Arg Phe Ser His Asp Val Thr Pro
            210                 215                 220 atc att ctg gct gcc cac tgc cag gaa tat gaa att gtg cat acc ctc    1141
Ile Ile Leu Ala Ala His Cys Gln Glu Tyr Glu Ile Val His Thr Leu
        225                 230                 235 ctg cgg aag ggt gct agg att gaa cgg cct cat gat tat ttc tgc aag    1189
Leu Arg Lys Gly Ala Arg Ile Glu Arg Pro His Asp Tyr Phe Cys Lys
    240                 245                 250 tgc aat gac tgc aac cag aaa cag aag cat gac tcg ttt agc cac tcc    1237
Cys Asn Asp Cys Asn Gln Lys Gln Lys His Asp Ser Phe Ser His Ser
255                 260                 265                 270 aga tct agg att aat gcc tat aaa ggc ctg gca agt ccg gct tac ctg    1285
Arg Ser Arg Ile Asn Ala Tyr Lys Gly Leu Ala Ser Pro Ala Tyr Leu
                275                 280                 285 tca ttg tct agt gaa gat cca gtc atg acg gct tta gaa ctt agc aat    1333
Ser Leu Ser Ser Glu Asp Pro Val Met Thr Ala Leu Glu Leu Ser Asn
            290                 295                 300 gaa ctg gca gtt ctg gcc aat att gag aaa gag ttc aag aat gac tac    1381
Glu Leu Ala Val Leu Ala Asn Ile Glu Lys Glu Phe Lys Asn Asp Tyr
        305                 310                 315 aaa aaa ctg tca atg cag tgc aaa gac ttt gtt gtt gga ctc ctt gat    1429
Lys Lys Leu Ser Met Gln Cys Lys Asp Phe Val Val Gly Leu Leu Asp
    320                 325                 330 ctg tgc aga aac act gaa gaa gtc gag gcc att ctg aat ggg gat gtt    1477
Leu Cys Arg Asn Thr Glu Glu Val Glu Ala Ile Leu Asn Gly Asp Val
335                 340                 345                 350 gaa acg ctc cag agt ggt gat cac ggt cgc cca aat ctc agc cgt tta    1525
Glu Thr Leu Gln Ser Gly Asp His Gly Arg Pro Asn Leu Ser Arg Leu
                355                 360                 365 aaa ctt gcc att aaa tat gaa gta aaa aaa ttt gta gct cat cca aac    1573
Lys Leu Ala Ile Lys Tyr Glu Val Lys Lys Phe Val Ala His Pro Asn
            370                 375                 380 tgc caa cag caa ctt ctc tcc att tgg tatgagaatc tttctggttt          1620
Cys Gln Gln Gln Leu Leu Ser Ile Trp
        385                 390 acgacagcag acaatggcgg tcaagttcct tgtggtcctt gctgttgcca ttggactgcc   1680
cttcctggct ctcatttact ggtttgctcc atgcagcaag atggggaaga taatgcgtgg   1740
accattcatg aagtttgtag cacacgcagc ctccttcacc attttctgg gactgctagt    1800 catgaatgca gctgacagat ttgaaggcac aaaactcctt cctaatgaaa ccagcacaga   1860
taatgcaaaa cagctgttca ggatgaaaac atcctgcttc tcatggatgg agatgctcat   1920
tatatcctgg gtaataggca tgatatgggc tgaatgtaaa gaaatctgga ctcagggccc   1980
caaggaatat ttgtttgagt tgtggaacat gcttgatttt ggtatgttag caattttcgc   2040
agcatcattc attgcgagat tcatggcatt ttggcatgct tccaaagccc agagcatcat   2100
tgacgcaaat gatactttga aggacttgac gaaagtaaca ttgggagaca atgtgaaata   2160
ctacaatttg gccaggataa agtgggaccc ctctgatcct caaataatat ctgaaggtct   2220
ttatgcaatt gctgtagttt taagtttctc taggatagct tatatttac agcaaatga    2280 aagctttgga cctctgcaga tatcacttgg aagaacagtc aaagacatct tcaagttcat   2340
ggtcatattc attatggtgt tgtggccctt tatgattgga atgttcaatc tctactccta   2400
ctacattggt gcaaaacaaa atgaagcctt cacaacagtt gaagagagtt ttaagacact   2460 gttctggggct atatttggac tttctgaagt gaaatcagtg gtcatcaact ataaccacaa   2520
```

```
attcattgaa acattggtt acgttcttta tggagtctat aatgttacga tggtcattgt    2580
tttgctaaat atgttaattg ccatgatcaa cagttcattc caggaaattg aggatgacgc    2640
tgatgtggag tggaaatttg caagggccaa actctggttt tcctactttg aggagggcag    2700
aacacttcct gtaccttcca atctggtgcc gagtccaaag tccctgtttt atctcttact    2760
gaagcttaaa aaatggattt ctgagctgtt ccagggccat aaaaaaggtt tccaggaaga    2820
tgcagagatg aacaagataa atgaagaaaa gaaacttgga attttaggaa gtcatgaaga    2880
cctttcaaaa ttatcacttg acaaaaaaca ggttgggcac aataaacaac caagtataag    2940
gagctcagaa gatttccatc taaatagttt caataatcct ccaagacaat atcagaaaat    3000
aatgaaaagg ctcattaaaa gatatgtact gcaggcccag atagataagg agagtgatga    3060
agtgaacgaa gggaactga aggaaattaa gcaggacatc tcaagtctcc gctatgaact    3120
ccttgaagaa aaatctcaga atacagaaga cctagcagaa cttattagag aacttggaga    3180
gaaattatcc atggaaccaa atcaagagga accaatagaa taatgcgaag acttccttag    3240
aaattcatat ttatttgtcc acttgaagcc atattatttt ctgatttatt ttcttaagtg    3300
ccaatgggcc cacctttttaa acaagaaaac gttaaataac ttgggccatc ctatcatctg    3360
gagccctagt atctaattt tttggtgatt aaactccatt gttcagggta aaggctgtag    3420
ataatgagga aaattatgcc cagttgtttg gtgcttgttt tataaactgc tttcttggat    3480
ataactaact cttgtgatga tgtcattgcc atgtagtgtc tgcctgaaaa tgggtcccag    3540
cggacagggg ctgacccacg ttactcccca tgcggttttt cctctgaagt ttatttcagg    3600
ttccttcttg cctgctctgt ggatcccctg ctggggactc ccagctctga aatttgggaa    3660
aaagtagccc atgggccttt agaatgcttt aatcctttct ttagaatgct gtttaaacac    3720
catttaccct acttatccct caatgcacat gattgatacc gttcatacaa aatggtctta    3780
catctatgta aaatttttctg attcatctat ttgaaaacat tacacttaac aatgaaaaaa    3840
gtttttcctc cactgaaccc tggaaacatg gtccagtttt gtgtgtgtgc gtgtgtgtaa    3900
atgtgtacac acagacataa agtacttgcc ctatttagtt tgtggctaat gtggacacac    3960
aaaagctctt tatgttataa atttttattg tcactaaaaa attttactgt ctaaataagt    4020
acctttatt ggagaaaaat caaaacccca acaaacact gtggttgttt ggttccatta    4080
tagcacaatt ttgtgccatt tctgggagca tttacagatg aatccccaca cttagccatt    4140
gaatgtaaag gggaaaaata aggtgagaat ttgtaaatac ttatctgtta ttttcaatat    4200
gttctatcct tctacccaaa tatataaaac aggaatttgc attcatgtgc atttaccaag    4260
aggttgttgt tgttacttac tgatcatgtg aagtggtgtc ttaaacaact aaaagcgatg    4320
aaggttcata tgtttactca agaccattg gcattcagag gatgctggac attaactgga    4380
actgctactt ccaattcaat aatgggagat ttcaaatgca aatctttaac ttcatcttaa    4440
agatgaaatg gttgcagaaa atctgtttag ctccaacttt ggcttaattt aaatcaaaga    4500
acatttatgt aaccagatca gaaaatacag ctgaaaattt ggaattcgag ctcggtaccc    4560
gggg                                                                4564
```

<210> SEQ ID NO 65
<211> LENGTH: 931
<212> TYPE: PRT
<213> ORGANISM: Homo sapiens

<400> SEQUENCE: 65

Met Ser Gln Ser Pro Ala Phe Gly Pro Arg Arg Gly Ser Ser Ser Arg

```
1               5                   10                  15
Gly Ala Ala Gly Ala Ala Arg Arg Asn Glu Ser Gln Asp Tyr Leu
            20                  25                  30
Leu Met Asp Ser Glu Leu Gly Glu Asp Gly Cys Pro Gln Ala Pro Leu
            35                  40                  45
Pro Cys Tyr Gly Tyr Tyr Pro Cys Phe Arg Gly Ser Asp Asn Arg Leu
            50                  55                  60
Ala His Arg Arg Gln Thr Val Leu Arg Glu Lys Gly Arg Arg Leu Ala
65                  70                  75                  80
Asn Arg Gly Pro Ala Tyr Met Phe Ser Asp Arg Ser Thr Ser Leu Ser
                85                  90                  95
Ile Glu Glu Glu Arg Phe Leu Asp Ala Ala Glu Tyr Gly Asn Ile Pro
                100                 105                 110
Val Val Arg Lys Met Leu Glu Glu Cys His Ser Leu Asn Val Asn Cys
                115                 120                 125
Val Asp Tyr Met Gly Gln Asn Ala Leu Gln Leu Ala Val Ala Asn Glu
                130                 135                 140
His Leu Glu Ile Thr Glu Leu Leu Lys Lys Glu Asn Leu Ser Arg
145                 150                 155                 160
Val Gly Asp Ala Leu Leu Leu Ala Ile Ser Lys Gly Tyr Val Arg Ile
                165                 170                 175
Val Glu Ala Ile Leu Ser His Pro Ala Phe Ala Glu Gly Lys Arg Leu
                180                 185                 190
Ala Thr Ser Pro Ser Gln Ser Glu Leu Gln Gln Asp Asp Phe Tyr Ala
                195                 200                 205
Tyr Asp Glu Asp Gly Thr Arg Phe Ser His Asp Val Thr Pro Ile Ile
                210                 215                 220
Leu Ala Ala His Cys Gln Glu Tyr Glu Ile Val His Thr Leu Leu Arg
225                 230                 235                 240
Lys Gly Ala Arg Ile Glu Arg Pro His Asp Tyr Phe Cys Lys Cys Asn
                245                 250                 255
Asp Cys Asn Gln Lys Gln Lys His Asp Ser Phe Ser His Ser Arg Ser
                260                 265                 270
Arg Ile Asn Ala Tyr Lys Gly Leu Ala Ser Pro Ala Tyr Leu Ser Leu
                275                 280                 285
Ser Ser Glu Asp Pro Val Met Thr Ala Leu Glu Leu Ser Asn Glu Leu
                290                 295                 300
Ala Val Leu Ala Asn Ile Glu Lys Glu Phe Lys Asn Asp Tyr Lys Lys
305                 310                 315                 320
Leu Ser Met Gln Cys Lys Asp Phe Val Val Gly Leu Leu Asp Leu Cys
                325                 330                 335
Arg Asn Thr Glu Glu Val Glu Ala Ile Leu Asn Gly Asp Val Glu Thr
                340                 345                 350
Leu Gln Ser Gly Asp His Gly Arg Pro Asn Leu Ser Arg Leu Lys Leu
                355                 360                 365
Ala Ile Lys Tyr Glu Val Lys Lys Phe Val Ala His Pro Asn Cys Gln
370                 375                 380
Gln Gln Leu Leu Ser Ile Trp Tyr Glu Asn Leu Ser Gly Leu Arg Gln
                385                 390                 395                 400
Gln Thr Met Ala Val Lys Phe Leu Val Val Leu Ala Val Ala Ile Gly
                        405                 410                 415
Leu Pro Phe Leu Ala Leu Ile Tyr Trp Phe Ala Pro Cys Ser Lys Met
                420                 425                 430
```

```
Gly Lys Ile Met Arg Gly Pro Phe Met Lys Phe Val Ala His Ala Ala
            435                 440                 445

Ser Phe Thr Ile Phe Leu Gly Leu Leu Val Met Asn Ala Ala Asp Arg
    450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
                485                 490                 495

Leu Ile Ile Ser Trp Val Ile Gly Met Ile Trp Ala Glu Cys Lys Glu
                500                 505                 510

Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
        530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
                565                 570                 575

Lys Tyr Tyr Asn Leu Ala Arg Ile Lys Trp Asp Pro Ser Asp Pro Gln
                580                 585                 590

Ile Ile Ser Glu Gly Leu Tyr Ala Ile Ala Val Val Leu Ser Phe Ser
        595                 600                 605

Arg Ile Ala Tyr Ile Leu Pro Ala Asn Glu Ser Phe Gly Pro Leu Gln
610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
                645                 650                 655

Ser Tyr Tyr Ile Gly Ala Lys Gln Asn Glu Ala Phe Thr Thr Val Glu
            660                 665                 670

Glu Ser Phe Lys Thr Leu Phe Trp Ala Ile Phe Gly Leu Ser Glu Val
        675                 680                 685

Lys Ser Val Val Ile Asn Tyr Asn His Lys Phe Ile Glu Asn Ile Gly
690                 695                 700

Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
                725                 730                 735

Asp Ala Asp Val Glu Trp Lys Phe Ala Arg Ala Lys Leu Trp Phe Ser
            740                 745                 750

Tyr Phe Glu Glu Gly Arg Thr Leu Pro Val Pro Phe Asn Leu Val Pro
        755                 760                 765

Ser Pro Lys Ser Leu Phe Tyr Leu Leu Leu Lys Leu Lys Lys Trp Ile
770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
            820                 825                 830

Lys Gln Pro Ser Ile Arg Ser Ser Glu Asp Phe His Leu Asn Ser Phe
            835                 840                 845
```

```
Asn Asn Pro Pro Arg Gln Tyr Gln Lys Ile Met Lys Arg Leu Ile Lys
    850                 855                 860

Arg Tyr Val Leu Gln Ala Gln Ile Asp Lys Glu Ser Asp Glu Val Asn
865             870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Glu Lys Leu Ser Met Glu Pro Asn Gln Glu Glu
        915                 920                 925

Thr Asn Arg
    930

<210> SEQ ID NO 66
<211> LENGTH: 10
<212> TYPE: DNA
<213> ORGANISM: Homo sapiens

<400> SEQUENCE: 66
tatcacttgg                                                          10

<210> SEQ ID NO 67
<211> LENGTH: 10
<212> TYPE: DNA
<213> ORGANISM: Homo sapiens

<400> SEQUENCE: 67
ttatttcagg                                                          10

<210> SEQ ID NO 68
<211> LENGTH: 15
<212> TYPE: PRT
<213> ORGANISM: Mus musculus

<400> SEQUENCE: 68

Arg Arg Asn Glu Ser Gln Asp Tyr Leu Leu Met Asp Glu Leu Gly
1               5                   10                  15
```